(12) United States Patent
Amar et al.

(10) Patent No.: US 7,361,735 B2
(45) Date of Patent: Apr. 22, 2008

(54) LITAF BINDING SITE PEPTIDES AND METHODS OF USING THE SAME

(75) Inventors: Salomon Amar, Brookline, MA (US); Xiaoren Tang, Winchester, MA (US)

(73) Assignee: Trustees of Boston University, Boston, MA (US)

( * ) Notice: Subject to any disclaimer, the term of this patent is extended or adjusted under 35 U.S.C. 154(b) by 261 days.

(21) Appl. No.: 10/796,947

(22) Filed: Mar. 10, 2004

(65) Prior Publication Data
US 2004/0219641 A1 Nov. 4, 2004

Related U.S. Application Data

(60) Provisional application No. 60/453,302, filed on Mar. 10, 2003.

(51) Int. Cl.
C07K 1/00 (2006.01)
A61K 38/16 (2006.01)
C12N 15/00 (2006.01)

(52) U.S. Cl. ...................................... 530/350; 530/358
(58) Field of Classification Search ..................... None
See application file for complete search history.

(56) References Cited

U.S. PATENT DOCUMENTS 6,077,693 A * 6/2000 Tang et al. ................. 435/69.5
6,566,501 B1 5/2003 Amar ......................... 530/350

FOREIGN PATENT DOCUMENTS

WO WO02086094 * 10/2002

OTHER PUBLICATIONS

Myokai et al., "A novel lipopolysaccharide-induced transcription factor regulating tumor necrosis factor α gene expression: Molecular cloning, sequencing, characterization, and chromosomal assignment," Proc. Natl. Acad. Sci. USA, 96:4518-4523 (1999).
Neumann et al., "Gene transfer into mouse lyoma cells by electroporation in high electric fields," EMBO J., 1(7):841-845 (1982).
Polyak et al., "A model for p53-induced apoptosis," Nature, 389(6648):300-305 (1997).
Smith and Waterman, "Comparison of Biosequences," Adv. Appl. Math. 2:482-489(1981).
Suganuma et al., "A New Process Of Cancer Prevention Mediated Through Inhibitor Of Tumor Necrosis Factor α Expression," Cancer Res., 56(16):3711-3715 (1996).
Sugarman et al., "Recombinant Human Tumor Necrosis Factor-α: Effects on Proliferation of Normal and Transformed Cells in Vitro," Science, 230(4728):943-945 (1985).
Talmadge et al., "Immunomodulatory Properties of Recombinant Murine and Human Tumor Necrosis Factor," Cancer Res., 48(3):544-550 (1988).
Tang et al., "Identification and functional characterization of a novel binding site on TNF-α promoter," Proc. Natl. Acad. Sci. USA, 100(7):4096-4101 (2003).
Uglialoro et al., "Identification of three new single nucleotide polymorphisms in the human tumor necrosis factor-α gene promoter," Tissue Antigens, 52(4):359-367 (1998).
Vousden and Lu, "Live or Let Die: The Cell's Response to p53," Nat. Rev. Cancer, 2(8):594-604 (2002).
Xaus et al., "LPS induces apoptosis in macrophages mostly through the autocrine production of TNF-α," Blood, 95(12):3823-3831 (2000).
Adams and Cory, "The Bcl-2 Protein Family: Arbiters of Cell Survival," Science, 281(5381):1322-1326 (1998).
Alexander et al., "Treatment with Recombinant Human Tumor Necrosis Factor-Alpha Protects Rats Against the Lethality, Hypotension, and Hypothermia of Gram-Negative Sepsis," J. Clin. Invest., 88:34-39 (1991).
Amar and Han, "Regulation of tumour necrosis factor-α gene expression," Appl. Genomics Proteomics 1(1):31-44 (2002).
Beutler and Cerami, "The Biology of Cachectin/TNF—A Primary Mediator of the Host Response," Ann. Rev. Immunol., 7:625-655 (1989).
Brugarolas et al., "Radiation-induced cell cycle arrest compromised by p21 deficiency," Nature, 377(6549):552-557 (1995).
Capecchi, M.R., "High Efficiency Transformation by Direct Microinjection of DNA into Cultured Mammalian Cells," Cell, 22(2 Pt. 2):479-488 (1980).
Cepko et al., "Construction and Applications of a Highly Transmissible Murine Retrovirus Shuttle Vector," Cell, 37(3):1053-1062 (1984).
Donis-Keller, H., "Phy M: an RNase activity specific for U and A residues useful in RNA sequence analysis," Nucleic Acids Res., 8(14):3133-3142 (1980).
Drouet et al., "Enhancers and transcription factors controlling the inducibility of the tumor necrosis factor-α promoter in primary macrophages," J. Immunol., 147(5):1694-1700 (1991).
El-Delry et al., "WAF1, A Potential Mediator of p53 Tumor Suppression," Cell, 75(4):817-825 (1993).
Felgner et al., "Lipofection: A highly efficient, lipid-mediated DNA-transfection procedure," Pro. Natl. Acad. Sci. USA, 84:7413-7417 (1987).
Galas and Schmitz, "DNAase footprinting: a simple method for the detection of protein-DNA binding specificity," Nucleic Acids Res., 5(9):3157-3170 (1978).

(Continued)

Primary Examiner—David Guzo
Assistant Examiner—Michele K. Joike
(74) Attorney, Agent, or Firm—Clark & Elbing LLP

(57) ABSTRACT

The invention provides molecules containing nucleic acid sequences for fragments of LPS-induced TNF-α factor (LITAF) and vectors containing these sequences. Also provided are molecules that contain the peptide sequence SQT-WREPGAAGSPFHL, or homologs thereof. Such molecules may be useful in the treatment of diseases that relate to the expression of TNF-α, where treatment involves the modulation of this expression. The invention also provides methods for identifying compounds that inhibit or enhance the transcription of TNF-α.

10 Claims, 14 Drawing Sheets

OTHER PUBLICATIONS

Graham and van der Eb, "A New Technique for the Assay of Infectivity of Human Adenovirus 5 DNA," *Virology*, 52(2):456-467 (1973).

Horng et al., "TIRAP: an adapter molecule in the Toll signaling pathway," *Nat. Immunol.*, 2(9):835-841 (2001).

IUPAC Commission on the Nomenclature of Organic Chemistry and IUPAC-IUB Commission on Biochemical Nomenclature, "Nomenclature of α-Amino Acids (Recommendations, 1974)," *Biochemistry* 14(2):449-462 (1975).

Kinzler and Vogelstein, "Life (and death) in a malignant tumour," *Nature*, 379(6560):19-20 (1996).

Ko and Prives, "p53: puzzle and paradigm," *Genes & Dev.*, 10(9):1054-1072 (1996).

Ksontini et al., "Disparate Roles for TNF-α and Fas Ligand in Concanavalin A-Induced Hepatitis," *J. Immunol.*, 160:4082-4089 (1998).

Levine, A.J., "p53, the Cellular Gatekeeper for Growth and Division," *Cell*, 88(3):323-331 (1997).

Li et al., "Nitric oxide-induced genotoxicity, mitochondrial damage, and apoptosis in human lymphoblastoid cells expression wild-type and mutant p53," *Proc. Natl. Acad. Sci. USA*, 99(16):10364-10369 (2002).

McClane et al., "Functional Consequences of Adenovirus-Mediated Murine Pancreatic Gene Transfer," *Hum. Gene Ther.*, 8(6):739-746 (1997).

Miyashita and Reed, "Tumor Suppressor p53 Is a Direct Transcriptional Activator of the Human Bax Gene," *Cell*, 80(2):293-299 (1995).

Morris et al., "A peptide carrier for the delivery of biologically active proteins into mammalian cells," *Nat. Biotechnol.*, 19(12):1173-1176 (2001).

Munshi et al., "Lipopolysaccharide-Induced Apoptosis of Endothelial Cells and Its Inhibition by Vascular Endothelial Growth Factor," *J. Immunol.*, 168(11):5860-5866 (2002).

\* cited by examiner (a) hLITAF/pGEX4T-1 constructs
1. hLITAF aa 1-228
2. hLITAF aa 1-75
3. hLITAF aa 1-151
4. hLITAF aa 76-151
5. hLITAF aa 76-228
6. hLITAF aa 152-228
7. hLITAF aa 152-228 Δ164-180
8. hLITAF aa 152-228 Δ181-195

(b) hTNF-α Promoter/pGL3-basic constructs
1. wt TNFP-pGL3basic (-991 to 1)
2. mtTNFP1-pGL3basic (-991 to 1 Δ-515 to -511)
3. mtTNFP2-pGL3basic (-550 to -487 plus TATA box)
4. mtTNFP3-pGL3basic (-550 to -487 Δ-515 to -511 plus TATA box)

-550                                    *****                                    -487
5'AGGCCTCAAGCCTGCCACCAAGCCCCCAGCTCCTTCTCCCCGCAGGGACCCAAACACAGGCCTCA-3'

FIG. 3

TNF-α promoter/pGL3basic constructs.
The binding site of transcription factor
on promoter is indicated by "☐"

<210> SEQ ID NO. 1
<211> LENGTH: 228
<212> TYPE: PRT
<213> ORGANISM: Homo Sapiens
<400> SEQUENCE: 1

| | | | | | | | | | |
|---|---|---|---|---|---|---|---|---|---|
| Met | Ser | Val | Pro | Gly | Pro | Tyr | Gln | Ala | Ala | 10 |
| Thr | Gly | Pro | Ser | Ser | Ala | Pro | Ser | Ala | Pro | 20 |
| Pro | Ser | Tyr | Glu | Glu | Thr | Val | Ala | Val | Asn | 30 |
| Ser | Tyr | Tyr | Pro | Thr | Pro | Pro | Ala | Pro | Met | 40 |
| Pro | Gly | Pro | Thr | Thr | Gly | Leu | Val | Thr | Gly | 50 |
| Pro | Asp | Gly | Lys | Gly | Met | Asn | Pro | Pro | Ser | 60 |
| Tyr | Tyr | Thr | Gln | Pro | Ala | Pro | Ile | Pro | Asn | 70 |
| Asn | Asn | Pro | Ile | Thr | Val | Gln | Thr | Val | Tyr | 80 |
| Val | Gln | His | Pro | Ile | Thr | Phe | Leu | Asp | Arg | 90 |
| Pro | Ile | Gln | Met | Cys | Cys | Pro | Ser | Cys | Asn | 100 |
| Lys | Met | Ile | Val | Ser | Gln | Leu | Ser | Tyr | Asn | 110 |
| Ala | Gly | Ala | Leu | Thr | Trp | Leu | Ser | Cys | Gly | 120 |
| Ser | Leu | Cys | Leu | Leu | Gly | Val | His | Ser | Gly | 130 |
| Leu | Leu | Leu | His | Pro | Leu | Leu | Arg | Gly | Cys | 140 |
| Pro | Ala | Gly | Arg | Gly | Pro | Leu | Leu | Ser | Gln | 150 |
| Leu | Gln | Ser | Ser | Pro | Gly | His | Leu | Gln | Ala | 160 |
| Phe | Val | Gly | Leu | Ser | Gln | Thr | Trp | Arg | Glu | 170 |
| Pro | Gly | Ala | Ala | Gly | Ser | Pro | Phe | His | Leu | 180 |
| Ser | Ser | Ser | Phe | Thr | Pro | Gly | Gly | Gly | Ser | 190 |
| Ala | Leu | Val | Val | Ser | Pro | Leu | Gln | Gly | Ala | 200 |
| His | Leu | His | Val | Phe | Phe | Trp | Gly | Glu | Tyr | 210 |
| Val | Ala | Lys | Leu | Thr | Asn | Leu | Gln | Thr | Pro | 220 |
| Glu | Ile | Ala | Ala | Trp | Ser | Arg | Ala | | | 228 |

FIG. 11

<210> SEQ ID NO. 2:
<211> LENGTH: 1773
<212> TYPE: DNA
<213> ORGANISM: Homo Sapiens
<400> SEQUENCE: 2

```
gtttctctcc ctgcccccgc gacttcgcgc aagatccggg aaggacaccc gaggcccctg   60
ggagaccctg gggaggtgaa agtcagagag cgaagcgggc cgtggcccct aggcctgacc  120
cctccccgcg gggtaaggcg ggcacccgc gagcgcaggg gtcctcttac tgctgatggc   180
acccagctct gggcccagac gccgctcacc gtccaccgcc ggtgctgggt aaaatgtcgg  240
ttccaggacc ttaccaggcg gccactgggc cttcctcagc accatccgca cctccatcct  300
atgaagagac agtggctgtt aacagttatt accccacacc tccagctccc atgcctgggc  360
caactacggg gcttgtgacg gggcctgatg ggaagggcat gaatcctcct tcgtattata  420
cccagccagc gcccatcccc aataacaatc caattaccgt gcagacggtc tacgtgcagc  480
accccatcac cttttggac cgccctatcc aaatgtgttg tccttcctgc aacaagatga  540
tcgtgagtca gctgtcctat aacgccggtg ctctgacctg gctgtcctgc gggagcctgt  600
gcctgctggg ggtgcatagc gggctgctgc ttcatcccct tctgcgtgga tgccctgcag  660
gacgtggacc attactgtcc caactgcaga gctctcctgg gcacctacaa gcgtttgtag  720
gactcagcca gacgtggagg gagccgggtg ccgcaggaag tcctttccac ctctcatcca  780
gcttcacgcc tggtggaggt tctgccctgg tggtctcacc tctccagggg gcccaccttc  840
atgtcttctt tggggggaa tacgtcgcaa aactaacaaa tctccaaacc cagaaattg   900
ctgcttggag tcgtgcatag gacttgcaaa gacattcccc ttgagtgtca gttccacggt  960
ttcctgcctc cctgagaccc tgagtcctgc catctaactg tgatcattgc cctatccgaa 1020
tatcttcctg tgatctgcca tcagtggctc ttttttcctg cttccatggg cctttctggt 1080
ggcagtctca aactgagaag ccacagttgc cttattttg aggctgttct gcccagagct 1140
cggctgaacc agcctttagt gcctaccatt atcttatccg tctcttcccg tccctgatga 1200
caaagatctt gccttacaga ctttacaggc ttggctttga gattctgtaa ctgcagactt 1260
cattagcaca cagattcact ttaatttctt aatttttttt ttaaatacaa ggaggggct  1320
attaacaccc agtacagaca tatccacaag gtcgtaaatg catgctagaa aaatagggct 1380
ggatcttatc actgccctgt ctccccttgt ttctctgtgc cagatcttca gtgcccattt 1440
ccatacaggg atttttttct catagagtaa ttatatgaac agttttatg acctcctttt  1500
ggtctgaaat acttttgaac agaatttctt tttttaaaa aaaacagag atgggtctt  1560
actatgttgc ccaggctggt gtcgaactcc tgggctcaag cgatccttct gccttggcct 1620
cccgaagtgc tgggattgca ggcataagct accatgctgg gcctgaacat aatttcaaga 1680
ggaggattta taaaccatt ttctgtaatc aaatgattgg tgtcattttc ccatttgcca 1740
atgtagtctc acttaaaaaa aaaaaaaaa aaa                               1773
```

FIG. 12

LITAF BINDING SITE PEPTIDES AND METHODS OF USING THE SAME

CROSS REFERENCE TO RELATED APPLICATIONS

This application claims priority under 35 U.S.C. 119 from provisional application U.S. Ser. No. 60/453,302 filed Mar. 10, 2003, the contents of which are incorporated herein by reference.

This invention was made with Government Support under Contract Number DE-14079, awarded by the National Institute of Cranofacial and Dental Research. The Government has certain rights in this invention.

BACKGROUND OF THE INVENTION

The present invention relates to the regulation of TNF-α expression by transcription factors that bind to a TNF-α promoter nucleotide sequence.

Tumor necrosis factor alpha (TNF-α) is a pleiotropic cytokine that is mainly produced by cells of the monocyte/macrophage lineage. TNF-α was originally identified as an endogenous factor, induced in response to inflammatory stimuli. Many studies have revealed that TNF-α exhibits both beneficial and pathologic effects and point to the importance of controlling the expression of this cytokine. For example, TNF-α and TNF-α-induced factors are known to contribute to the pathogenesis of inflammatory disorders (Alexander et al., J. Clin. Invest. 88:34-39, 1991; Sugarman et al., Science. 22:943-945, 1985; Beutler & Cerami, Annu. Rev. Immunol. 7:625-655, 1989; Talmadge et al., Cancer Res. 48:544-550, 1988; and Uglialoro et al., Tissue Antigens 52:359-367, 1998). The regulation of TNF-α gene expression in cells of the monocytic lineage is stimulus-dependent and quite complex, involving controls at both transcriptional and post-transcriptional levels. Many studies on the transcriptional regulation of TNF-α have focused on the investigation of transcription factors that bind to the responsive element sites within the TNF-α promoter, such as nuclear factor kappa B (NF-κB), Ets, NF-AT, activating protein-1 (AP1), cAMP response element binding protein (C/EBP) LPS-induced TNF-α factor (LITAF) and signal transducers and activators of transcription (STAT1). However, the relative contributions of these various regulatory elements in transcriptional activation of the TNF-α gene in human monocytes are poorly known.

Lipopolysaccharide (LPS), extracted from the outer membrane of Gram-negative bacteria, has been identified as a principal endotoxic component. LPS is a potent stimulator of monocytes and macrophages, inducing production and secretion of TNF-α and other inflammatory. The effects of LPS on transcription factor activity and expression have been widely investigated. Previous studies suggested that in vivo, LPS up-regulates the DNA binding activity of inducible transcription factors NF-κB, AP-1, and C/EBP in a time-dependent manner, but it down-regulates the DNA binding activity of constitutive transcription factors Sp1 and AP-2. The human TNF-α (hTNF-α) promoter contains motifs that resemble NF-κB-binding sites; however, controversy exists as to the involvement of NF-κB in TNF-α gene regulation. These sequences do not seem to be necessary for virus or LPS induction, nor do they appear to be able to stimulate virus or LPS induction alone. However, it has been suggested that NF-κB is an important factor in TNF-α gene transcription in LPS-challenged monocytes and macrophages. NF-κB-binding motifs are found in the hTNF-α promoter region and were shown to translocate into the nuclei of LPS-stimulated monocytes. In mice, mutation(s) or deletion(s) of NF-κB-binding motifs on the TNF-α promoter failed to show reporter gene activation in transfected cells. However, in humans, TNF-α promoter activity in transfected cell lines was found to be independent of the NF-κB-binding motifs. Drouet et al., J. Immunol. 147:1694-1700, 1991, offered an explanation for these conflicting data, suggesting that enough NF-κB is constitutively expressed to sustain high-level baseline expression of the human TNF-α gene compared with the mouse. An alternative explanation is that there may be another transcription factor acting independently or in concert with NF-κB in the activation of hTNF-α transcription.

In U.S. Pat. No. 6,566,501, such a factor is described. This polypeptide, termed liposaccharide-induced TNF-α factor (LITAF), was found to bind to the DNA-binding domain located from −550 to −487 in the promoter region of the human TNF-α gene. Furthermore, inhibition of human LITAF (hLITAF) mRNA expression in THP-1 cells resulted in a reduction of hTNF-α transcripts. It was also found that high levels of hLITAF mRNA are expressed predominantly in the placenta, peripheral blood leukocytes, lymph nodes, and the spleen.

SUMMARY OF THE INVENTION

The present invention describes a peptide fragment derived from the full-length sequence of LITAF that interacts with a promoter of the human TNF-α gene. DNA-footprinting experiments show that this interaction protects the promoter nucleotides CTCCC (−515 to −511) from DNase degradation. Furthermore, interaction of LITAF fragments with this TNF-α promoter results in an enhancement of TNF-α transcription.

Accordingly, in a first aspect, the invention features a molecule having a nucleic acid sequence of from 48 to 1770 nucleotides, and substantially identical to a corresponding nucleic acid sequence of SEQ ID NO. 2, that encodes a fragment of the peptide corresponding to SEQ ID NO. 1, or a homolog thereof, wherein the fragment or homolog enhances TNF-α transcription by interacting with a TNF-α promoter nucleotide sequence. Preferably, the nucleic acid sequence encodes the LSQTWREPGAAGSPFHL (SEQ ID NO: 3) peptide sequence.

In another aspect, the invention features a molecule having a nucleic acid sequence encoding the LSQTWREPGAAGSPFHL (SEQ ID NO: 3) peptide sequence, or a homolog thereof. In an embodiment of any of the nucleic acid sequences or expression constructs of the present invention, the sequence encodes a LITAF DNA binding domain for the hTNF-α promoter region, preferably nucleotides CTCCC (−515 to −511).

In another aspect, the invention features a vector that includes a molecule having a nucleic acid sequence of the invention, i.e., those encoding a fragment of the peptide corresponding to SEQ ID NO. 1, or a homolog thereof, as described above, or those encoding a LSQTWREPGAAGSPFHL (SEQ ID NO: 3) peptide sequence. Preferably, the vector is a viral vector, and most preferably is selected from the group consisting of adenoviral vectors, adeno-associated virus (AAV) vectors, retroviral vectors, hybrid adenovirus-AAV vectors, and herpes-simplex virus (HSV) vectors. The invention also features an expression construct that contains a nucleic acid sequence encoding a fragment of the peptide corresponding to SEQ ID NO. 1 or a host cell containing this nucleic acid sequence.

In another aspect, the invention features a peptide fragment of the peptide SEQ ID NO. 1, whereby said fragment enhances TNF-α transcription by interacting with a TNF-α promoter nucleotide sequence, preferably hTNF-α. In one example, the peptide fragment includes the SQTWREP-GAAGSPFHL sequence (SEQ ID NO: 5). In another example, the peptide is SQTWREPGAAGSPFHL (SEQ ID NO: 5), or a homolog thereof. In other examples, the peptide fragment includes an allelic variant of the SQTWREP-GAAGSPFHL sequence (SEQ ID NO: 5) or a variant that contains a conservative amino acid substitution for a residue of this sequence, where the variant retains the ability to interact with a TNF-α promoter nucleotide sequence. These variants can include those peptides that are the result of C-terminal, N-terminal, both N- and C-terminal, or interior deletions of the full-length LITAF peptide sequence.

In another aspect, the invention features a method of identifying compounds that inhibit LITAF binding to a TNF-α promoter region that includes: a) incubating a mixture of a molecule containing a LSQTWREPGAAGSPFHL peptide sequence (SEQ ID NO: 3) (component 1); a molecule that includes a TNF-α promoter region (component 2), and the test compound (component 3); b) measuring the extent of binding of component 1 to component 2 in the absence of component 3; measuring the extent of binding of component 1 to component 2 in the presence of component 3); and determining the ratio of the binding measured in step c) to that measured in step b), wherein a decrease of binding in step c) relative to step b) indicates that the test compound inhibits the binding of LITAF to the TNF-α promoter region ion.

In another aspect, the invention features a method of identifying compounds that enhance LITAF binding to a TNF-α promoter region that includes: a) incubating a mixture of a molecule containing a LSQTWREPGAAGSPFHL peptide sequence (SEQ ID NO: 3) (component 1), wherein said molecule is not full-length LITAF; a molecule that includes the TNF-α promoter region (component 2), and the test compound (component 3); b) measuring the extent of binding of component 1 to component 2 in the absence of component 3; measuring the extent of binding of component 1 to component 2 in the presence of component 3); and determining the ratio of the binding measured in step c) to that measured in step b), wherein an increase of binding in step c) relative to step b) indicates that the test compound enhances the binding of LITAF to the TNF-α promoter region ion.

In a preferred embodiment of any of the compound-identifying methods of the invention, the peptide containing the SQTWREPGAAGSPFHL sequence (SEQ ID NO: 5) and the nucleic acid having the promoter region are not brought into contact with each other in step a) before exposing one of these components to the test compound. In another preferred embodiment, the molecule containing the LSQTWREPGAAGSPFHL sequence (SEQ ID NO: 3) is not full-length LITAF. In yet another embodiment, the TNF-α promoter region having a CTCCC nucleic acid sequence (SEQ ID NO: 4).

In another aspect, the invention features an antibody which binds to a LITAF fragment that contains the LSQT-WREPGAAGSPFHL peptide sequence (SEQ ID NO: 3).

In another aspect, the invention features a method of suppressing tumor cell growth in an animal that includes administering a vector that includes a nucleic acid sequence of the invention, i.e., those encoding a fragment of the peptide corresponding to SEQ ID NO. 1, or a homolog thereof, or those encoding a LSQTWREPGAAGSPFHL peptide sequence (SEQ ID NO: 3). Preferably, the vector is a viral vector, and most preferably is selected from the group consisting of adenoviral vectors, adeno-associated virus (AAV) vectors, retroviral vectors, hybrid adenovirus-AAV vectors, and herpes-simplex virus (HSV) vectors. In one embodiment, the tumor is a solid tumor, preferably of a cancer selected from the group consisting of non-small cell lung carcinoma, prostate carcinoma, renal carcinoma, colon carcinoma, ovarian carcinoma, pancreatic carcinoma and melanoma. In another embodiment, the method further includes determining if the tumor cell is deficient in p53.

By "aa" is meant amino acid sequence.

By "fragment" of a protein or peptide sequence is meant a peptide that does not include the uninterrupted full length sequence. Preferred fragments include those peptides resulting from the deletion of one or more internal amino acid residues (i.e., those that are not C-terminal or N-terminal), peptides resulting from the deletion of one or more residues from the C-terminus (i.e., C-terminally truncated), or peptides resulting from the deletion of one or more residues from the N-terminus (i.e., N-terminally truncated). Compounds and methods of the present invention can also include derivatives of such molecules. Derivatives are amino acid sequences formed from the native compounds either directly, or by modification or partial substitution. Analogs are those amino acid sequences that have a structure similar to, but not identical to, the native compound, differing in respect to certain components or side chains. Analogs may be synthetic or from a different evolutionary origin and may have a similar or opposite metabolic activity when compared to wild-type. Derivatives, or analogs of the nucleic acids or peptides of the invention include, but are not limited to, molecules having regions that are substantially homologous to the nucleic acids or peptides of the invention, in various embodiments, by at least about 70%, 80%, 85%, 90%, 95%, 98%, or even 99% identity (with a preferred identity of 80-99%) over a nucleic acid or amino acid sequence of identical size, or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman, Adv. Appl. Math., 2:482-489, 1981.

By "full-length LITAF" or "LITAF," each of are used interchangeably herein, is meant a peptide having SEQ ID NO. 1 or a peptide homologous to SEQ ID NO. 1. By "hLITAF is meant human LITAF, i.e., a peptide having SEQ ID NO. 1.

By "homologs" are meant two nucleic acid or peptide sequences that have similar, or "homologous", nucleotide or amino acid sequences, respectively. When applied to LITAF, or a peptide fragment thereof, the term "homolog" encompasses peptides whose amino acids correlate to those amino acids of SEQ ID NO. 1 by sequence number but which differ by the inclusion of conservative amino acid substitutions at one or more positions. When applied to nucleotide sequence encoding LITAF, or fragments thereof, the term "homolog" includes allelic variants, orthologs, paralogs of the nucleotide sequence defined herein by SEQ ID NO. 2, or those degenerate nucleotide sequences of SEQ ID NO. 2 that encode LITAF, or fragments thereof. Homologous nucleotide sequences encode those sequences coding for isoforms of LITAF or LITAF fragments. Isoforms can be expressed in different tissues of the same organism as a result of, e.g., alternative splicing of RNA. Alternatively, isoforms can be encoded by different genes. In the invention, homologous nucleotide sequences include nucleotide sequences encoding for a LITAF protein fragment of species other than humans, including, but not limited to, mammals, and thus can include, e.g., mouse, rat, rabbit, dog, cat, cow, horse, and other organisms. Homologous nucleotide sequences also include, but are not limited to, naturally-occurring allelic variations and mutations of the nucleotide sequences set forth herein.

By "polypeptide" or "peptide," as used interchangeably herein, is meant a molecule that includes natural or unnatural amino acid residues joined by amide bonds formed between a carboxyl group of one amino acid and an amino group from the next one. As used herein, for the most part, the names of naturally-occuring amino acids and aminoacyl residues used herein follow the naming conventions suggested by the IUPAC Commission on the Nomenclature of Organic Chemistry and the IUPAC-IUB Commission on Biochemical Nomenclature as set out in Nomenclature of α-Amino Acids (Recommendations, 1974), Biochemistry, 14(2), (1975). Accordingly, the abbreviations "Ala" or "A," "Arg" or "R," "Asn" or "N," "Asp" or "C," "Gln" or "Q," "Glu" or "E," "Gly" or "G" "His" or "H," "Ile" or "I," "Leu" or "L," "Lys" or "K," "Met" or "M," "Phe" or "F," "Pro" or "P," "Ser" or "S," "Thr" or "T," "Trp" or "W," "Tyr" or "Y," and "Val" or "V" refer to the amino acids alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine and their corresponding aminoacyl residues in peptides in their L-, D- or D, L-forms. Where no specific configuration is indicated, one skilled in the art would understand that the stereochemistry of the α-carbon of the amino acids and aminoacyl residues in peptides described herein is the naturally occuring or "L" configuration with the exception of the achiral molecule glycine and with the further exception of any amino acids which are achiral or otherwise designated as "D-."

By "promoter" is meant a nucleic acid sequence sufficient to direct transcription, wherein such elements may be located in the 5' or 3' regions of the native gene.

By "substantially identical" is meant a peptide or nucleic acid sequence exhibiting at least 75%, but preferably 82%, more preferably 89%, most preferably 94%, or even 99% identity to a reference peptide or nucleic acid sequence. For peptides, the length of comparison sequences will generally be at least 10 amino acids, and preferably at least 16 amino acids. For nucleic acids, the length of comparison sequences will generally be at least 60 nucleotides, preferably at least 90 nucleotides, and more preferably at least 120 nucleotides.

BRIEF DESCRIPTION OF THE DRAWINGS

FIG. 3 depicts the sequence of TNF-α promoter DNA from nt −550 to −487 (SEQ ID NO: 47). Note that the hLITAF-binding site is indicated by a dotted line along the top of the sequence.

FIG. 4a includes a probe consisting of $[^{32}P]$ATP-labeled hTNF-α promoter DNA from −550 to −487 was added to each tube of reaction buffer. Shown: probe alone (lane 1) and mixed with 50 fold excess of unlabeled competitor (lane 4, 6 and 8), 0.1 µg GST-fusion protein alone (lane 2), 0.1 µg GST-hLITAF aa 1-151 (lane 3 and 4), 152-228 (lane 5 and 6), 1-228 (lane 7 and 8). The only shifted DNA band is indicated by an arrow. FIG. 4b includes a [32 P]ATP labeled TNF-α promoter DNA from −550 to −487 (lanes 1, 3, 5, 7, 10, 13, and 16), or mutant DNA from −550 to −487Δ−515 to −511 as probe was added to each tube of reaction buffer (lanes 2, 4, 6, 9, 12, and 15). The probed DNAs were mixed with 50 fold excess of unlabeled competitor (lanes 8, 11, 14 and 17). The probe was also individually mixed with 0.1 µg GST-fusion protein alone (lanes 2-3), 0.1 µg GST-hLITAF fusion protein aa 1-151 (lane 4-5), 152-228 (lanes 6-8), 1-228 (lanes 9-11), 152-228Δ164-180 (lanes 12-14), and 152-228Δ181-195 (lanes 15-17) and then, incubated on ice for 30 min prior to electrophoresis on non-denaturing 6% polyacrylamide gel. Only the shifted DNA band is indicated by an arrow.

FIG. 6a depicts the activity measured due to either the promoter wtTNFβ (−991 to 1) or mtTNFβ1 (−991 to 1Δ−515 to −511). pGL3-basic transfected cell as unstimulated control was used. After transfection of DNAs for 3 hrs, the cells were washed with PBS twice, and stimulated with 100 ng/ml LPS (E. coli) or transfected with Chariot/peptide complex of 1 μg/ml of either peptide A, B, C, or HA. Triplicate assays were performed. Values were normalized by β-gal production and graphed. FIG. 6b depicts the activity measured due to the promoter mtTNFβ2 (−550 to −487 plus TATA box) or mtTNFβ3 (−550 to −487Δ−515 to −511 plus TATA box). LPS or peptides as stimuli and controls were used at the same condition as described above.

FIG. 7a shows the western blot analysis was performed using cell lysates from COS-7 cells which were treated with 100 or 500 ng/ml of LPS for 4 or 24 hrs. 60 μg of crude cell lysate was loaded per lane and separated on an 8% SDS-PAGE, which were then transferred to Immobilon-P. The protein blots were probed individually with monoclonal antibodies specific for p53 (DO-1, Santa cruz) or with goat polyclonal antibodies for actin (C-11, Santa cruz). p53 proteins were expressed well in lanes 2 through 4. No detectable band was found in lane 1, demonstrating a threshold affected by both quantity of LPS stimulation and duration of exposure in induction of p53. FIG. 7b shows the transcripts for LITAF in WTK-1 or COS-7 cells, which were detected by Northern blot. Cells were incubated with 100 or 500 ng/ml of LPS for 4 or 24 hrs. Total cellular RNA was purified by using the Oligotex mRNA Kit (Qiagen). mRNA was size-fractionated on a denaturing formaldehyde-agarose gel (1.1%) and transferred onto a Hybond-N+ membrane (Amersham). These filters were hybridized with an γ-$^{32}$P ATP-labeled DNA probe and then autoradiographed with BIOMAX MR film (Kodak).

FIG. 9a shows that GST alone and GST-LITAF fusion proteins were stained with Coomassie brilliant blue R-250. FIG. 9b depicts the results of the EMSA assay. Specifically, a reaction mixture containing 0.1 μg GST-hLITAF fusion protein, 1 μl radiolabeled (1×10$^5$ cpm/μl) double stranded oligonucleotide DNA (2 pmol), 3 mg poly (dI/dC), 5 mg bovine serum albumin, 4 μl gel shift binding 5× buffer (Promega), and nuclease-free water to 20 μl, was incubated at RT for 30 min prior to electrophoresis on non-denaturing 6% polyacrylamide gels in Tris-borate-EDTA buffer (90 mM Tris-borate, 2 mM EDTA HEPES [pH 8.0]).

FIG. 11 shows the peptide sequence of human LITAF (SEQ. ID NO. 1).

FIG. 12 shows the nucleotide sequence the encodes human LITAF. (SEQ. ID NO. 2).

DETAILED DESCRIPTION

Figure 2:
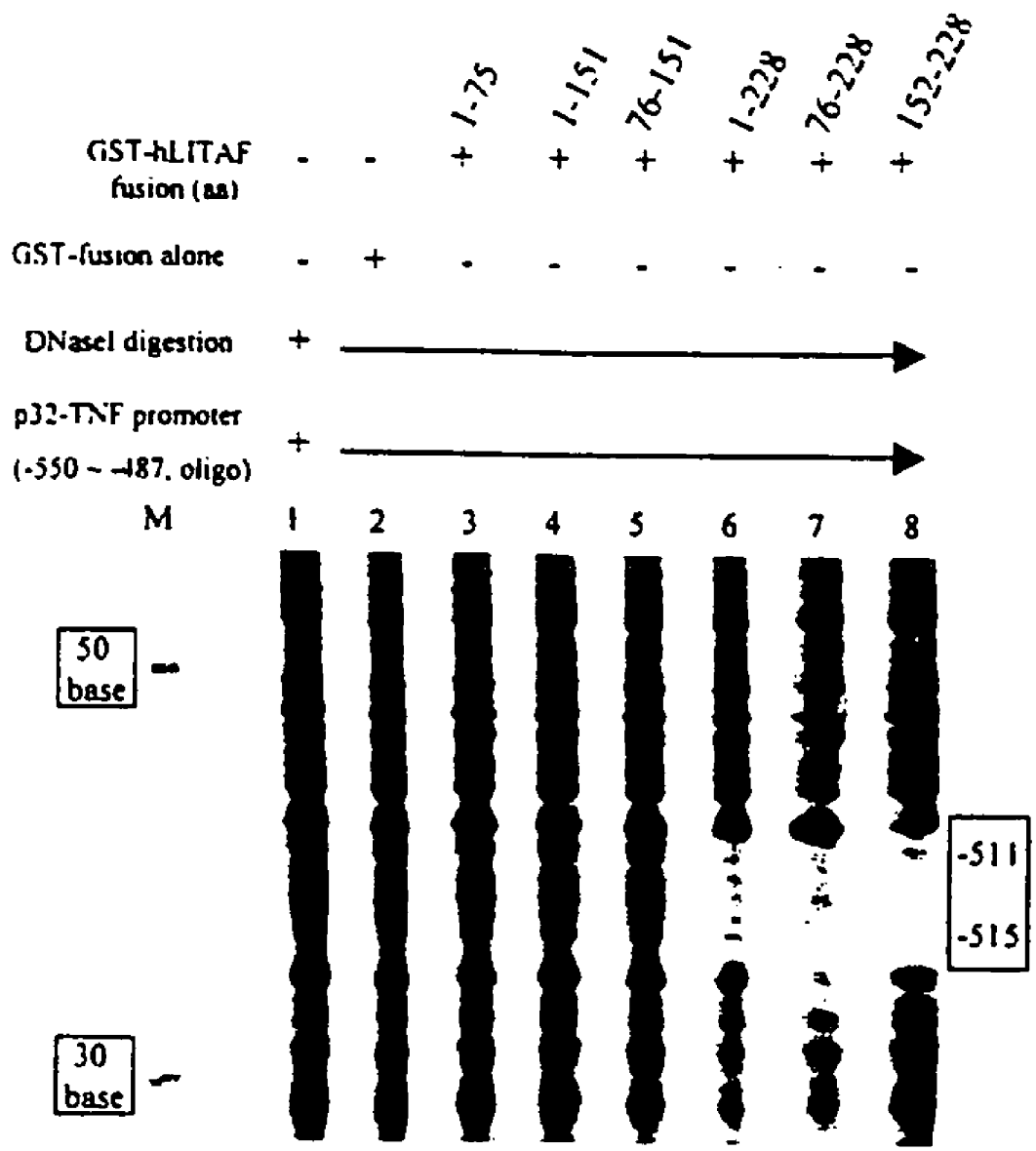
FIG. 2 is an illustration of the results of a Dnase I footprinting assay used to detect hLITAF/hTNF-α DNA interaction. Lanes 1 to 8 all contain an ATP-labeled TNF-α promoter DNA (−550 to −487) probe, added to each tube of reaction buffer. However, lanes 3 to 8 also were mixed with a GST-hLITAF fusion protein. Lane 1 does not contain any protein (i.e., it is a non-protein lane). Lane 2 contains 0.1 µg of a GST-fusion protein. Lane 3 contains 0.1 µg of the GST-hLITAF fusion protein (aa 1-75) depicted in FIG. 1a. Lane 4 contains 0.1 µg of the GST-hLITAF fusion protein (aa 1-151) depicted in FIG. 1a. Lane 5 contains 0.1 µg of the GST-hLITAF fusion protein (aa 76-151) depicted in FIG. 1a. Lane 6 contains 0.1 µg of the GST-hLITAF fusion protein (aa 1-228) depicted in FIG. 1a. Lane 7 contains 0.1 µg of the GST-hLITAF fusion protein (aa 76-228) depicted in FIG. 1a. Lane 8 contains 0.1 µg of the GST-hLITAF fusion protein (aa 152-228) depicted in FIG. 1a. $[^{32}P]$ATP-labeled DNAs, 30 bp, 50 bp and 70 bp, were used as markers on the left side of gel and those marker MW values were indicated as shown (lane M). The protected, undigested DNA is in the gap, indicated by a box on the right side of the gel. The DNase I-degraded DNA was measured base by base in comparison with markers.
Figure 4A:
FIGS. 4a and 4b depict Electrophoresis Mobility Shift Assays (EMSA) of protein/DNA-interaction.
Figure 4B:
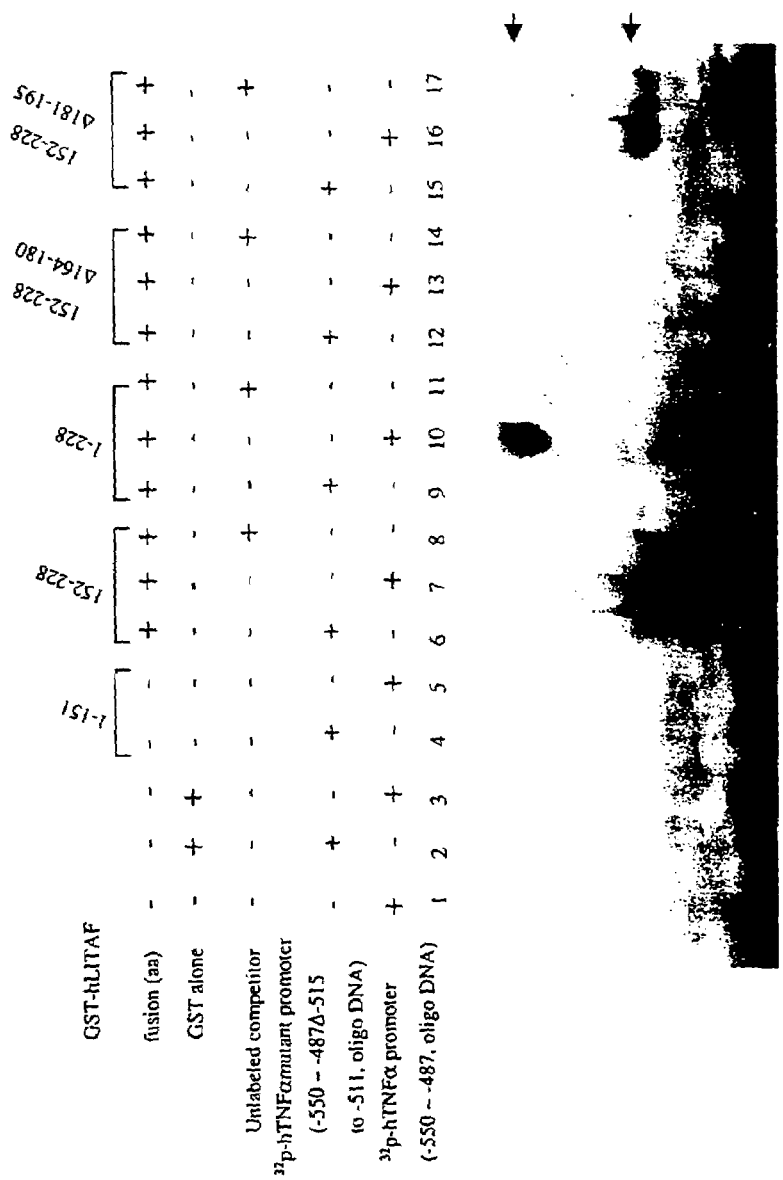

In the present invention, a novel regulatory element, located within the hTNF-α promoter, is defined that mediates LPS-induced TNF-α gene expression in THP-1 cells. DNase I footprinting demonstrated that hTNF-α promoter DNA sequences, located between −515 to −511, were protected by hLITAF-protein. As demonstrated herein, sequence analysis identified the protected bases as CTCCC (see FIG. 2b). Comparison of CTCCC to all other known regulatory elements by database analysis indicates that this DNA is a unique regulatory element. Human TNF-α promoter DNA could not be protected from DNase I-digestion by peptides corresponding to hLITAF residues 1-75, 1-151 or 76-151 (FIG. 2a, lanes 3, 4 and 5, respectively), but DNA was protected by peptides that include LITAF residues 1-228, 76-228, or 152-228 (FIG. 2a, lane 6, 7 and 8, respectively). In addition, deletion of the CTCCC DNA sequence dramatically reduced hLITAF/TNF-α binding (FIG. 4b, lane 6 and 9, respectively).

A novel hLITAF peptide sequence (residues 164-180 of SEQ ID NO. 1) that plays an important role for binding activity is also identified in the present invention. As shown herein, deletion of residues 164-180 from the LITAF or LITAF sequence fragments abolished hLITAF binding to DNA (FIG. 4b, lane 13), suggesting that this region of LITAF is an important contributor to the modulation of TNF-α transcription. As also shown herein, this peptide can physically interact with CTCCC in vitro (FIG. 4a, lanes 5 and 7).

TNF-α is an important cytokine that plays a role in host defense. The cytokine is produced primarily in macrophages and monocytes in response to infection, invasion, injury, or inflammation. Some examples of inducers of TNF-α include bacterial endotoxins, bacteria, viruses, lipopolysaccharide (LPS) and cytokines including GM-CSF, IL-1, IL-2 and IFN-γ. In addition, TNF-α can be involved in apoptotic processes in which undesirable cells are eliminated via programmed cell death. Hence, the enhancement of TNF-α transcription and, potentially, expression may ameliorate undesirable biological responses such as, for example, an autoimmune response.

Despite the protective effects of the cytokine, overexpression of TNF-α often results in disease states, particularly in infectious, inflammatory and autoimmune diseases. True to the pleiotropic nature of this cytokine, these processes may also involve the apoptotic pathways (Ksontini, R., et al., J. Immunol, 160:4082-4089, 1998). High levels of plasma TNF-α have been found in infectious diseases such as sepsis syndrome, bacterial meningitis, cerebral malaria, and AIDS; autoimmune diseases such as rheumatoid arthritis, inflammatory bowel disease (including Crohn's disease), sarcoidosis, Kawasaki syndrome, graft-versus-host disease and transplant (allograft) rejection; and organ failure conditions such as adult respiratory distress syndrome, congestive heart failure, acute liver failure and myocardial infarction. Other diseases in which TNF-α is involved include asthma, brain injury following ischemia, non-insulin-dependent diabetes mellitus, insulin-dependent diabetes mellitus, hepatitis, atopic dermatitis, multiple sclerosis, and pancreatitis. Furthermore, inhibitors of TNF-α have been suggested to be useful for cancer prevention (Suganuma, M. et al., Cancer Res. 56:3711-3715, 1996). Elevated TNF-α expression may also play a role in obesity. Therefore, an agent that dampens or reduces TNF-α transcription and, potentially, expression may be useful for the treatment of the above-mentioned diseases or maladies.

Nucleic Acid Sequences Encoding LITAF Fragments

In one aspect, the present invention provides a method of modulating gene expression of TNF-α by administering to the cell a nucleic acid sequence that encodes a LITAF peptide fragment, which binds to a TNF-α nucleic acid promoter and modulates TNF-1 transcription. In one embodiment, transcription is enhanced. In another embodiment, transcription is suppressed.

The nucleic acid sequences of the present invention or portions thereof can be inserted into a vector used to propagate the sequences in a cell. Such vectors are introduced into cells (e.g., prokaryotic or eukaryotic), and the cells are propagated to produce multiple copies of the vector. A useful type of vector is an expression vector. Coding regions of the nucleic acid sequences of the present invention or fragments thereof can be inserted into an expression vector under conditions appropriate for expression of the sequences. Such vectors, are introduced into cells (e.g., prokaryotic or eukaryotic cells) under conditions appropriate for expression. The expressed protein is purified from the cells by routine methods. In one embodiment, the cell is eukaryotic (e.g., mammalian, avian, insect, or yeast). In a preferred embodiment, the cell is human.

The invention thus provides nucleic acid constructs which encode the various LITAF peptide fragments of this invention, various DNA vectors containing those constructs for use in transducing prokaryotic and eukaryotic cells, cells transduced with the nucleic acids, fusion proteins encoded by the above nucleic acids, and target gene constructs.

Each of the nucleic acids of this invention may further contain an expression control sequence operably linked to the coding sequence and may be provided within a DNA vector, e.g., for use in transducing prokaryotic or eukaryotic cells. Some or all of the nucleic acids of a given composition, including any optional nucleic acids, may be present within a single vector or may be apportioned between two or more vectors. In certain embodiments, the vector or vectors are viral vectors useful for producing recombinant viruses containing one or more of the nucleic acids. The recombinant nucleic acids may be provided as inserts within one or more recombinant viruses which may be used, for example, to transduce cells in vitro or cells present within an organism, including a human or non-human mammalian subject. For example, LITAF-related nucleic acids may be present within a single recombinant virus or within a set of recombinant viruses, each of which containing one or more of the set of recombinant nucleic acids. Viruses useful for such embodiments include any virus useful for gene transfer, including adenoviruses, adeno-associated viruses (AAV), retroviruses, hybrid adenovirus-AAV, herpes viruses, lenti viruses, etc. In specific embodiments, the recombinant nucleic acid containing the target gene is present in a first virus and one or more or the recombinant nucleic acids encoding the transcription regulatory protein(s) are present in one or more additional viruses. In such multiviral embodiments, a recombinant nucleic add encoding a fusion protein containing a bundling domain and a transcription activation domain, and optionally, a ligand binding domain, may be provided in the same recombinant virus as the target gene construct, or alternatively, on a third virus. It should be appreciated that non-viral approaches (naked DNA, liposomes or other lipid compositions, etc.) may be used to deliver nucleic acids of this invention to cells in a recipient organism.

The invention also provides methods for rendering a cell capable of regulated expression of a target gene which involves introducing into the cell one or more of the nucleic acids of this invention to yield engineered cells which can express the appropriate fusion protein(s) of this invention to regulate transcription of a target gene. The recombinant nucleic acid(s) may be introduced in viral or other form into cells maintained in vitro or into cells present within an organism. The resultant engineered cells and their progeny containing one or more of these recombinant nucleic acids or nucleic acid compositions of this invention may be used in: a variety of important applications, including human gene therapy, analogous veterinary applications, the creation of cellular or animal models (including transgenic applications) and assay applications. Such cells are useful, for example, in methods involving the addition of a ligand, preferably a cell permeant ligand, to the cells (or administration of the ligand to an organism containing the cells) to regulate expression of a target gene. Particularly important animal models include rodent (especially mouse and rat) and non-human primate models. In gene therapy applications, the cells will generally be human and the peptide sequence of each of the various domains present in the fusion proteins (with the possible exception of the bundling domain) will preferably be, or be derived from, a peptide sequence of human origin.

Polypeptide LITAF Fragments

In another aspect, the present invention provides a method of modulating gene expression of TNF-α by administering to the cell a LITAF peptide fragment, which binds to a TNF-α nucleic acid promoter sequence and either enhances or dampens TNF-α transcription.

Isolated LITAF peptide fragments can be produced recombinantly from the corresponding fragment of the nucleic acid encoding such peptides or, alternatively, can be chemically synthesized using techniques known in the art such as conventional solid phase Fmoc or t-Boc chemistry, as described, for example, in Bodanszky, "The Principles of Peptide Synthesis", Hather, Rees, Trost, Lehn, Schleyer, Zabradnik, Eds., Springer-Verlag, Berlin, 1984. The fragments so produced can be tested to identify those which can either to enhance or inhibit TNF-α transcription by interaction with the TNF-α promoter nucleotides CTCCC (−515 to −511), such as by microinjection assays. In an illustrative embodiment, LITAF peptide fragments containing a SQTWREPGAAGSPFHL peptide sequence (SEQ ID NO: 5) can be tested for their ability to enhance TNF-α transcription in a cell-based assay.

It is also possible to modify the structure of a LITAF peptide fragment for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the LITAF peptide fragments described in more detail herein. Such modified peptide can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the binding of the peptide to the TNF-α promotor. Conservative replacements or substitutions are those that take place within a family of amino acids that are related in their side chains, and apply to those that result from genetically encoding or those that are synthetically produced. Amino acids can be divided into four families: (1) acidic residues, such as aspartatic acid or glutamic acid; (2) basic residues, such as lysine, arginine, or histidine; (3) nonpolar residues, such as alanine, valine, leucine, isoleucine, proline, phenylalanine, methionine, or tryptophan; and (4) uncharged polar residues, such as glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic residues, such as aspartate, glutamate; (2) basic residues, such as lysine, arginine histidine, (3) aliphatic residues, such as glycine, alanine, valine, leucine, isoleucine, serine, threonine, with serine and threonine optionally be grouped separately as aliphatic-hydroxyl; (4) aromatic residues, such as phenylalanine, tyrosine, tryptophan; (5) amide residues, such as asparagine, glutamine; and (6) sulfur-containing residues, such as cysteine and methionine (see, for example, Biochemistry, 2nd ed., Ed. by L. Stryer, W H Freeman and Co.: 1981). Alternatively, amino acid replacement can be based on steric criteria, e.g. isosteric replacements, without regard for polarity or charge of amino acid sidechains.

Thus, one or more amino acid residues in a LITAF protein fragment, can be replaced with another amino acid residue from the same family. Alternatively, in another embodiment, mutations can be introduced randomly along all or part of a nucleic acid encoding a LITAF protein fragment, such as by saturation mutagenesis, and the resultant mutants can be screened for their ability to bind to TNF-α promoter region to identify mutants that retain activity. Following mutagenesis of the nucleic acid encoding the LITAF protein fragment can be expressed by any recombinant technology known in the art, and the activity of the protein can be determined.

LITAF Fragments for Screening Biologically Active Compounds

As discussed herein, it is important to be able to tightly regulate the expression of TNF-α by either up-regulation or down-regulation. The present invention features a method of identifying compounds that inhibit LITAF binding to a TNF-α promoter region that includes: a) incubating a mixture of a molecule containing a LSQTWREPGAAGSPFHL peptide sequence (SEQ ID NO: 3) (component 1); a molecule that includes a TNF-α promoter region (component 2), and the test compound (component 3); b) measuring the extent of binding of component 1 to component 2 in the absence of component 3; measuring the extent of binding of component 1 to component 2 in the presence of component 3); and determining the ratio of the binding measured in step c) to that measured in step b), wherein a decrease of binding in step c) relative to step b) indicates that the test compound inhibits the binding of LITAF to the TNF-α promoter region ion.

In contrast to methods described herein that relate primarily to the identification of compounds having the ability to interfere with LITAF binding to the TNF-α promoter (down-regulation of TNF-α), it is also possible to up-regulate TNF-α levels using a variety of methodologies. The present invention also features a method of identifying compounds that enhance LITAF binding to a TNF-α promoter region that includes: a) incubating a mixture of a molecule containing a LSQTWREPGAAGSPFHL peptide sequence (SEQ ID NO: 3) (component 1), wherein said molecule is not full-length LITAF; a molecule that includes the TNF-α promoter region (component 2), and the test compound (component 3); b) measuring the extent of binding of component 1 to component 2 in the absence of component 3; measuring the extent of binding of component 1 to component 2 in the presence of component 3); and determining the ratio of the binding measured in step c) to that measured in step b), wherein an increase of binding in step c) relative to step b) indicates that the test compound enhances the binding of LITAF to the TNF-α promoter region ion.

A number of these methodologies can be applied in vivo, systemically or locally, in a complex biological system such as a human. For example, increased copy number of LITAF- or LITAF fragment-encoding nucleic acid in expressible form (by DNA transfection), could be employed. A screening system for the identification of a compound that enhances the binding of LITAF, or LITAF fragment, to the TNF-α promoter can be designed in a manner similar to the screening assay described previously for the identification of compounds that interfere with this binding.

High-throughput screening of compound libraries in an effort to identify a small organic molecule having a desired molecular interaction/effect, is an increasing common approach to drug discovery and lead optimization. Such compound libraries are available from commercial sources such as ComGenex (U.S. Headquarters, South San Francisco, Calif.), Maybridge (Cornwall, UK), and SPECS (Rijswijk, Netherlands).

Compound screening or assay development is usually performed on semi-automated workstations or on fully-automated robots, such as the Tecan Genesis 200 platform. Assays can be developed for a variety of 96/384 well liquid handling equipment capable of both normal or low volume assay formats. In the design of new assays for drug discovery screening, fluorescence-based detection technologies are particularly well-suited to high-throughput applications.

Such technologies can be applied to the identification of compounds that interfere with the productive binding of LITAF, or a functionally active fragment of LITAF, to the TNF-α promoter. The term "productive binding" refers to binding of LITAF to the TNF-α promoter that results in increased transcription of TNF-α (this is the "productive" event). The phrase "functionally active fragment of LITAF" refers to a fragment of LITAF which has the ability to productively bind the TNF-α promoter.

Generally speaking, the identification of such a compound is accomplished by introducing candidate molecules from a compound library, independently, into an incubation mixture containing: 1) a portion of the TNF-α promoter which is sufficient to exhibit specific binding to LITAF when contacted with the LITAF under conditions appropriate for specific binding; and 2) LITAF, or a functionally active fragment of LITAF. Many formats which can be developed for such a binding assay are known to one skilled in the art.

In one example, the TNF-α promoter portion can be fixed to a substrate (e.g., the wells of a 96-well microtitre plate) using conventional attachment techniques. A directly labeled (e.g., $S^{35}$-Methionine or $S^{35}$-Cysteine) LITAF fragment or a LITAF fragment that is further conjugated to a reporter group (e.g., a fluorescent group or an affinity group, such as biotin) is then incubated with the TNF-α promoter portion either together with (experimental) or in the absence of (positive control) a candidate compound. Following the incubation period, the wells of the microtiter plate are washed to remove non-specifically bound LITAF fragment. Label retained in the well of the microtiter plate following the wash step represents labeled LITAF fragment specifically bound to the TNF-α promoter. By comparing the extent of specific binding relative to controls (e.g., positive and negative controls), it is possible to identify compounds which interfere with the binding of LITAF to the TNF-α promoter. A substantial reduction in the label retained in an experimental well, relative to the positive control well, is an indication that the candidate drug-like compound included in the experimental well effectively interferes with the binding of LITAF fragment to the TNF-α promoter.

In preferred embodiments, the candidate compound screening is carried out robotically. Given the fact that "productive" binding of a LITAF fragment results in an increase in transcription of the TNF-α gene, the screening process lends itself to the use of a reporter gene fusion, linked operatively to the TNF-α promoter. Particularly useful reporter genes encode, for example, firefly luciferase or the jelly green fluorescence protein (GFP), the latter of which is detectable by ELISA methodologies. Signal from the luciferase reporter can be measured using an inexpensive luminometer, or thousands of samples may be measured simultaneously using sophisticated CCD luminometers. BD Biosciences has reported the expression of luciferase protein from T7 sites using in vitro transcription and translation (using the Promega, TNT Quick Coupled Transcription/Translation System). In view of this, a particularly convenient format for high-throughput screening of a candidate drug-like molecule for its ability to interfere with the binding of a LITAF fragment to the TNF-α promoter would feature the fusion of the TNF-α promoter to a nucleic acid sequence encoding the luciferase reporter. Such a construct could be added to all wells of microtiter plate. Individual candidate drug-like compounds are also added to specifically addressed wells. A LITAF fragment is then added to all experimental wells of the plate. One skilled in the art will recognize that the order of addition of LITAF fragment and the TNF-α promoter construct can be exchanged as long as the two specifically interacting molecules (i.e., LITAF fragment and the TNF-α promoter fragment) are not combined prior to the addition of a candidate drug-like compound.

A system, such as the Promega in vitro transcription/translation system referenced above, is then employed to generate the luciferase reporter in those wells in which productive binding of LITAF or LITAF fragment to the TNF-α promoter construct takes place. As discussed above, the luciferase signal is detectable in a high-throughput format using a CCD luminometer. Given the fact that no wash step would be required in such an assay format, it is not necessary to attach any of the components of the reaction to the wells of the microtiter plate. In preferred embodiments, the TNF-α promoter construct includes nucleotides CTCCC (−515 to −511) of the TNF-α promoter. As demonstrated herein, these nucleotides are protected by LITAF in a DNase I protection study.

In addition to using a cell-free system for identifying compounds having the ability to interfere with or enhance the binding of LITAF or a LITAF fragment to the TNF-α promoter, a cell-based screening system can also be employed. THP-1 cell cultures are particularly well-suited to such an assay. Briefly, the mammalian cells are plated and transfected (by conventional techniques) with a TNF-α promoter-driven reporter construct. Again, the reporter moiety can be, for example, green fluorescence protein or luciferase. LITAF, or a LITAF fragment is also introduced into the cell, together with the compound to be tested.

One method for introducing proteins or peptides into the cells of a mammalian cell culture is the Chariot™ reagent (Morris et al., Nature Biotechnology 19:1173-1176, 2001; available from Active Motif, Carlsbad, Calif. This reagent quickly and efficiently delivers biologically active proteins, peptides and antibodies directly into cultured mammalian cells at an efficiency of 60-95%. Less than two hours after delivery, live cells can be assayed to determine the effects of the introduced materials, without the need for fixing. In addition to the introduction of LITAF or LITAF fragments into the cultured cells, the use of this reagent also aids in the cellular uptake of the compound to be screened, as well as reporter construct. The Chariot reagent can be used in the presence or absence of serum and is independent of the endosomal pathway, which can modify macromolecules during internalization. Additionally, the use of this method for introducing a protein or peptide bypasses the transcription-translation process, which reduces the time required to complete the assay from overnight to less than two hours.

One of skill in the art will recognize that other forms of transfection can be used to introduce LITAF or LITAF fragments into cultured cells. Such techniques include, for example, the use of cationic liposomes (Felgner et al., Proc. Natl. Acad. Sci. USA 84:7413-7417, 1987), calcium phosphate coprecipitation (Graham and van der Eb, Virology 52:456-457, 1973), electroporation (Neumann, EMBO J. 7:841-845, 1982), microinjection (Capecchi, Cell 22:479-488, 1980), and viral vectors (Cepko et al., Cell 37:1053-1062, 1984).

The present invention also features a method for stimulating p53 production in a cell. The disclosed method for stimulating p53 production requires contacting the cell with subclinical levels of LPS to stimulate and thereby supplement the tumor in question with p53. The decision as to whether subclinical levels of LPS are established locally, or systemically, is dependent primarily on the pathology to be treated. Clinical levels of LPS associated, for example, with Gram-negative bacterial infection, is on the order of 5-10 μg/ml in circulation. The term "subclinical levels", as used herein, refers to effective levels which are at least about 10-fold lower than these clinical levels.

As also described herein, LPS did not induce LITAF transcription in p53-deficient cells, under the same experimental conditions that caused LITAF induction in p53 wild-type cells. As reported in Example 2 below, analysis of LPS-induced apoptotic cells by using TdT mediated dUTP-biotin nick end labeling method (TUNEL) indicated DNA fragmentation in COS-7 cells treated with 500 ng/ml of LPS. Given the fact that in many cancer tumors p53 is found either lacking or deficient, cancer patients with documented p53 deficiency could be treated with other agents involved in the enhanced expression of TNF-α. Therefore, the invention features suppressing tumor cell growth in an animal by tumor cells in the animal with LITAF, LITAF fragments, compounds that stimulate LITAF production, including the vectors described herein, or compounds that enhance TNF-α transcription via binding to the TNF-α promoter at −515 to −511.

Methods

Bacterial Strains

All expression constructions including mutagenesis were performed using *E. coli* strain DH5α (Invitrogen). Specifically, all clones involved in the purification of any GST fusion proteins were performed in strain BL21 (Pharmacia).

Cell Culture

The human monocytic cell line, THP-1, was maintained in RPMI 1640 medium supplemented with 10% fetal bovine serum [all from GIBCO, Gaithersburg, Md.], and maintained in an atmosphere of 5% $CO_2$ at 37° C.

Plasmid Constructs

A. Generation of hLITAF DNA Fragments

The series of hLITAF DNA fragments were generated by PCR with the following primer pairs and subcloned into the pGEX4T-1 vector (Pharmacia) (FIG. 1a): 1. Glutathione S-transferase (GST) hLITAF aa 1-75: 5'-CGGGATCCAT-GTCGGTTCCAGG ACCT-3' (SEQ ID NO: 6) and 5'-cggaattcggtaattggattgttatt-3' (SEQ ID NO: 7); 2. GST-hLITAF aa 1-151: 5'-CGGGATCCAT GTCGTTCCAGGACCT-3' (SEQ ID NO: 8) and 5'-cggaattccagttgggacagtaatgg-3' (SEQ ID NO: 9); 3. GST-hLITAF aa 76-151: 5'-CGGGATCCGT-GCAGACGGTCTACGTG-3' (SEQ ID NO: 10) and 5'-cggaattccagttgggacagtaatgg-3' (SEQ ID NO: 11'); 4. GST-hLITAF aa 1-228: 5'-CGGGATCCATGTCGGTTCCAGGACCT-3' (SEQ ID NO: 12) and 5'-cgggatcctcagggtctca gggaggc-3' (SEQ ID NO: 13); 5. GST-hLITAF aa 76-228: 5'-CGGGATCCGT-CAGACGGTCTACGTG-3' (SEQ ID NO: 10) and 5'-cgg-gatcctcagggtctcagggaggc-3' (SEQ ID NO: 13); 6. GST-hLITAF aa 152-228: 5'-CGGGATCCCAGAGCTCT CCTGGGCAC-3' (SEQ ID NO: 14) and 5'-cgggatcct-cagggtctcagggaggc-3' (SEQ ID NO: 13); 7. GST-hLITAF aa 152-228Δ181-195. The first in-frame mutant hLITAF DNA fragment was generated by PCR with primer pairs: 5'-CGG-GATCCGGACCATTACTGTCCCAA-3' (SEQ ID NO: 15) (coordinates 435-456 bp with BamHI) and 5'-ccaaaagaaga-catggctggat gagaggtg-3' (SEQ ID NO: 16) (coordinates 621-531 bp). The second hLITAF DNA fragment was generated by PCR with primer pairs: 5'-CATGTCT-TCTTTTGGGGG-3' (SEQ ID NO: 17) (coordinates 609 to 624 bp) and 5'-cgggatcctcagggtct cagggaggc-3' (SEQ ID NO: 13) (coordinates 983-966 bp with EcoRI).

Both the first and second DNA fragments were purified and diluted as template to 1 ng/reaction, and amplified by PCR with primer pairs: 5'-CGGGATCCGGACCATTACTG TCCCAA-3' (SEQ ID NO: 15) (coordinates 435-456 bp with BamHI) and 5'-cgggatcctcagggtctcagggaggc-3' (SEQ ID NO: 13) (coordinates 983-966 bp with EcoRI). Finally, the in-frame hLITAF mutant DNA fragment was inserted into the pGEX4T-1 vector; 8. GST -hLITAF aa 152-228Δ164-180. The first in-frame mutant hLITAF DNA fragment was generated by PCR with primer pairs: 5'-CGG-GATCCGG ACCATTACTGTCCCAA-3' (SEQ ID NO: 15) (coordinates 435-456 bp with BamHI) and 5'-tccaccag-gcgtga atcctacaaacgcttg-3' (SEQ ID NO: 18) (coordinates 564 to 477 bp). The second hLITAF DNA fragment was generated by PCR with primer pairs: 5'-TTCACGCCTG-GTGGAGGT-3' (SEQ ID NO: 19) (coordinates 552 to 570 bp) and 5'-cgggatcctcagggtctcagggaggc-3' (SEQ ID NO: 13) (coordinates 983-966 bp with EcoRI). Both first and second DNA fragments above were purified and diluted as template to 1 ng/reaction, and amplified by PCR with 5' and 3' primers, 5'-CGGGATCCGGACCATTACTGTCCCAA-3' (SEQ ID NO: 15) (coordinates 435-456 bp with BamHI) and 5'-cgggatcctcagggtctcagggaggc-3' (SEQ ID NO: 13) (coordinates 983-966 bp with EcoRI). Finally, the in-frame mutant DNA fragment was inserted into the vector.

Subcloning the hLITAF DNA Fragments into a pGL3-Basic Expression Construct

The following series of hTNF-α promoter DNA fragments were subcloned (FIG. 1b) into the pGL3-Basic vector, which has a promoterless and enhancerless luciferase reporter gene, available from Pharmacia: 1. wtTNFP (−991 to 1) was generated by PCR with primer pairs: 5'-AGCTC-CTGG GAGATATGGCCAC-3' (SEQ ID NO: 20') and 5'-gggtgtgccaacaactgccttt-3'(SEQ ID NO: 21'). 2. mtTNFP1 (−991 to 1Δ−515 to −511). The first in-frame mutant hTNF-α promoter was generated by PCR with primer pairs, 5'-AGCTCCTGGGAGATATGGCCAC-3'(SEQ ID NO: 20) and 5'-tgcgaaggagctgggggctt (SEQ ID NO: 22). The second mutant DNA was generated by PCR with primer pairs, 5'-CCTTCGCAGGGACCCAAACACAGGCCTCA-3' (SEQ ID NO: 23) and 5'-gggtgtgccaacaactgccttt-3' (SEQ ID NO: 21). Both first and second DNA fragments above were purified and diluted as template to 1 ng/reaction and finally amplified by PCR with primer pairs, 5'-AGCTCCTGG-GAGATATGGCCAC-3' (SEQ ID NO: 20) and 5'-gggtgtgc-caacaactgccttt-3' (SEQ ID NO: 21). 3. mtTNFP2 (−550 to −487 plus TATA Box) was generated by annealing with primer pairs: 5'-AGGCCTCAAGCCT GCCACCAAGC-CCCCAGCTCCTTCTCCCCGCAGGGAC-CCAAACACAGGCCTCATATA AAGGCAGTTGTTG-GCACACCC-3' (SEQ ID NO: 24) and 5'-gggtgtgccaacaactgcctttatatgaggcctgtgtttgggtccctg cggg-gagaaggagctgggggcttggtggcaggc ttgaggcct -3' (SEQ ID NO: 25). 4. mtTNFP3 (−550 to −487Δ−515 to −511 plus TATA Box) was generated by annealing with primer pairs: 5'-AG-GCCTCAAGCCTGCC ACCAAGCCCCCAGCTCCT-TCGCAGGGACCCAAACACAGGCCT-CATATAAAGGCAGT TGTTGGCACACCC-3' (SEQ ID NO: 26) and 5'-gggtgtgccaacaactgcctttatat-gaggcctgtgtttgggtccctgcgaaggagctgggg gcttggtggcaggct-tgagg cct-3' (SEQ ID NO: 27).

Purification of GST-hLITAF Fusion Protein

GST-hLITAF recombinant plasmids were transformed into competent BL21 cells. LBA medium (2 ml) was inoculated with a single colony of the appropriate transformant for culture at 37° C. overnight. This 2 ml culture was then transferred to 100 ml of 2×YTA broth plus ampicillin (100 μg/ml) and grown at 30° C. with shaking until the absorbance at 600 nm reached 0.6, at which time IPTG was added to a final concentration of 0.1 mM. The culture was incubated for an additional 2-6 hrs, then subjected to centrifugation at 3,000×g for 10 min at 4° C. The cells were washed with PBS and completely suspended in 2 ml of ice-cold PBS, then lysed by brief sonication for 10 sec (output 20, Branson Sonifier 450), then centrifuged twice at 5,000×g for 10 min at 4° C. The supernatant was transferred to a fresh container, to which was added 100 μl of Glutathione-Sepharose 4B beads (Pharmacia) and the mixture was rocked for 30 min at 4° C., then washed three times with PBS. Protein samples were run in 10% SDS-PAGE.

DNase I Footprinting

The protein-DNA binding site was analyzed by the DNase I footprinting method (Galas and Schmitz, Nucleic Acids Res. 5:3157-3170, 1978) with some modifications. Two oligonucleotides were synthesized. The first one was designed as a template, with a HindIII site at the 5' end. For the reverse orientation, nucleotides from −487 to −550 bp in the hTNF-α promoter were represented (5'-TGAGGCCT-GTGTTTGGGTCCCTGCGGGGAGAAG-GAGCTGGGGGCTTGGTGGCAGG CTTGAGGCCT-3' (SEQ ID NO: 28). The second one was designed as a primer from −550 to −535 bp in the hTNF-α promoter, 5'-aggcct-caagcctgcc-3' (SEQ ID NO: 29). Template (0.5 µg) and 0.1 µg primer were mixed and incubated at 37° C. for 1 hr, then 2 µl 2.5 mM 4dNTP mix, 5 µl 10×Klenow fragment buffer, 5 units Klenow fragment (Invitrogen), and water to 50 µl were added, and incubated at 37° C. for 30 mm. The DNA was purified, then precipitated with ethanol. After centrifugation, the DNA pellet was suspended in 10 µl TB buffer. DNA (0.5 µg) was labeled with γ-[$^{32}$P]ATP using T4 polynucleotide kinase (Promega) and then digested by HindIII as previously described (Donis-Keller, H., Nucl. Acids Res. 8:3133, 1980). Labeled DNA was purified using a G-25 Sephadex column (Boehringer) and precipitated with ethanol. After centrifugation, the DNA pellet was suspended in 10 µl water. The γ-[$^{32}$P]ATP-labeled DNA was then mixed with 25 µl binding buffer (Promega), 0.1 µg GST-hLITAF fusion protein (GST fusion protein alone as control), and nuclease-free water (Promega) to 50 µl, incubated on ice for 30 mm, to which 50 µl pre-warmed $Ca^2/Mg^2$ solution at RT was added and incubated for one min, then 3 µl DNase I (Promega) was added, mixed gently, incubated for an additional 5 min, followed by reaction termination. The reaction mixture was treated with phenol and precipitated with ethanol. After centrifugation, the DNA pellet was suspended in 5 µl of TE buffer. The sample was applied to a 6% polyacrylamide sequencing gel (Invitrogen).

Electrophoresis Mobility Shift Assay

A reaction mixture containing 0.1 µg GST-hLITAF fusion protein, 1 µl radiolabeled (1×10$^5$ cpm/µl) double stranded DNA oligonucleotide (2 pmol), 3 µg poly(dI/dC), 5 µg bovine serum albumin, 4 µl gel shift binding 5×buffer (Promega), and nuclease-free water to 20 µl, was incubated at RT for 30 min prior to electrophoresis on non-denaturing 6% polyacrylamide gels in Tris-borate-EDTA buffer (90 mM Tris-borate, 2 mM EDTA HEPES [pH8.0]).

Peptides

Figure 1:
FIGS. 1a and 1b are diagrams of expression constructs embodied by the present invention. These constructs were used for the production of GST fusion protein (FIG. 1a) and for Luciferase reporter assay (FIG. 1b). Three LITAF protein fragments, designated A, B or C, were synthesized and respectively indicated by a box at the region of hLITAF (FIG. 1a). The major potential binding site for transcription factors was indicated by a box on the hTNF-α promoter DNA (FIG. 1b).
Figure 5:
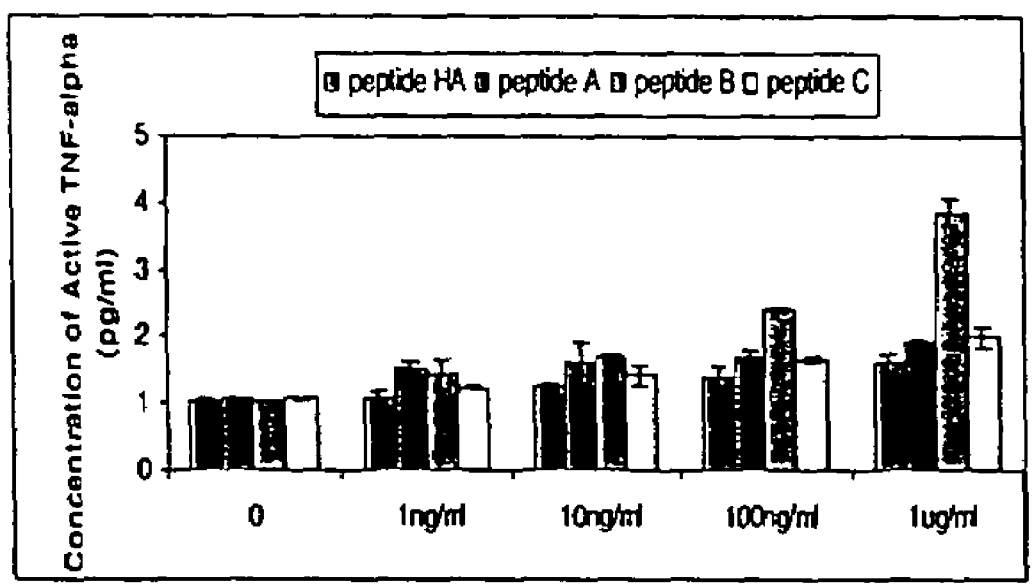
FIG. 5 is a graphical representation of the production of TNF-α in THP-1 cells after transfection of peptide A, B, C, or HA with Chariot as described herein. The concentration of active of TNF-α was induced by various concentrations of peptide and measured by duplicate ELISA tests at the same condition and graphed.

The following synthetic peptides were supplied by Lofstrand Labs Ltd (Gaithersburg, Md.): Peptide A consisted of the sequence (SYYTQPAPIPNNNPIT VQTVY; SEQ ID NO: 30) from the hLITAF aa 60-80; peptide B consisted of the sequence (SQTWREPGAAGSPFHL; SEQ ID NO: 5) from aa 165 to 180; and peptide C consisted of the sequence (LSSSFTPGGGSALVVS; SEQ ID NO: 31) from aa 180 to 195 (FIGS. 1, 4, and 5). Hemagglutinin antigenic peptide (HA) served as control peptide and consisted of the sequence (YPYDVPDYASL: SEQ ID NO: 32). All peptides were solubilized in DMSO and delivered into THP-1 cells by Chariot kit (Chariot Motif, 1914 Palomar Oaks Way, Suite 150, Carlsbad, Calif. 92008) for reporter assays as described in references Homg et al., Nature Immunology 2:835-841, 2001; Morris et al., Nat. Biotechnol. 19:1173-6, 2001.

ELISA

THP-1 cells were induced to maturation by addition of 200 mM PMA (Sigma) and incubated at 37° C., 5% $CO_2$ for 20 hrs, then washed with PBS twice, and stimulated (delivered) with Chariot/peptide complex of various concentrations of either peptide A or B or C or HA in a 96-well plate at 2×10$^4$ cells/well as indicated in the text. After 24 hrs of incubation at 37° C., 5% $CO_2$, culture supernatants were harvested, centrifuged at 1,500×g to remove cell debris, then TNF-α was measured by ELISA (ABRAXIS, Hatboro, Pa.) and quantified on a Model 680 Microplate Reader (BioRad).

Transient Transfection and Luciferase Assay

THP-1 cells (5×10$^6$/well) were induced to maturation by addition of 200 mM PMA (Sigma) and incubated at 37° C., 5% $CO_2$ for 20 hrs, washed with PBS twice, co-transfected with 1 µg DNAs by using Fugene 6 (Roche Molecular Biochemicals) for 3 hrs, washed with PBS, then individually transfected with Chariot/peptide complex of 1 µg/ml peptide A, B, C or HA or stimulated with 100 ng/ml LPS (*E. coli*) for 3 hrs, washed with PBS, incubated at 37° C., 5% $CO_2$, overnight. The β-galactosidase gene was included in all transfections. The cells were harvested and lysed approximately 12 hrs after transfection. Luciferase activity in the lysates was measured using a commercial kit (Luciferase Reporter Assay System, Promega) and normalized by β-gal assay in the same lysates as described (McClane et al., Hum. Gene Ther. 10:739-746, 1997).

Example 1

The following experiments were performed to clarify the mechanism of hLITAF/hTNF-α interaction, as well as to identify and characterize the regulatory elements responsible for LITAF's contribution to hTNF-α regulation.

Determination of hLITAF-Binding Site by Footprint Analysis

The site within the hTNF-α promoter that binds LITAF was determined by DNase I footprinting. In this experiment, six wild-type or mutant GST-hLITAF fusion proteins were used, as shown in FIG. 1a. The [$^{32}$P]ATP labeled hTNF-α promoter DNA fragment (−550 to −487) was used as the probe. In order to label this probe only at one end from its 5' flank, the DNA was designed to contain a HindIII site at its 3' flank. HindIII-digestion thus removed the [$^{32}$P]ATP label at the 3' end, leaving a probe labeled only at its 5' end. The DNA was then degraded base by base from its 3' end by DNase I digestion, but protected from degradation by its protein-DNA interaction (gap), and the surviving fragments were detected by electrophoresis and autoradiography. As shown in FIG. 1a, the clone GST-hLITAF aa 1-228 expressed the full-length LITAF peptide sequence, whereas other clones expressed various deletion mutants. The probed DNA was fully degraded by DNase I in the presence of GST alone, or in the presence of fusion proteins containing LITAF aa 1-75, 76-151, or 1-151 (FIG. 2a, lanes 3, 4, and 5, respectively), but was partially protected by fusion proteins containing LITAF aa 1-228, 76-228 or 152-228 (FIG. 2a, lanes 6, 7, and 8, respectively). These results indicate that the LITAF aa 1-151 does not contain the site of LITAF-DNA binding. Furthermore, the promoter region, about 5 bases in length, that was protected from DNase activity appeared to contain a "CTCCC" motif, corresponding to −515 to −511 (see FIG. 2b).

Identification of Binding Activity of the Short Sequence, CTCCC, in the Human TNF-α Promoter Three GST-hLITAF fusion proteins containing LITAF aa 1-151, 152-228, or 1-228, or GST alone as control, were used in EMSA binding experiments to [$^{32}$P]ATP-labeled hTNF-α promoter DNA containing the CTCCC sequence. It was observed that CTCCC motif bound to a peptide sequence within hLITAF aa 152-228, as fusion proteins containing LITAF aa 152-228 or 1-228 shifted the DNA band, as indicated by arrows in FIG. 4a, lanes 5 and 7, respectively, whereas no band shift was observed in with GST alone (lane 2) for or for the fusion protein containing LITAF aa 1-151 (lane 3). To further demonstrate binding activity by the short sequence CTCCC in hTNF-α promoter, two mutants were constructed in which the CTCCC region was deleted (see FIG. 1b). In EMSA experiments run under identical conditions, the fusion proteins containing LITAF aa 1-151, 152-228 or 1-228 failed to bind to the mutant DNA probes (FIG. 4b, lanes 4, 6, and 9, respectively). As a positive control, fusion proteins containing LITAF aa 152-228 or 1-228 were found to shift the wild type probe containing the CTCCC motif (FIG. 4b, lanes 7 and 10, respectively). These results indicate that the CTCCC motif of the TNF-α promoter region is a hLITAF binding site.

The CTCCC binding region within the hLITAF aa 152-228 was defined further. GST-hLITAF fusion proteins containing internal deletions (aa 152-228Δ181-195 and 152-228Δ164-180) were created, as shown in FIG. 1a. Their analysis by EMSA is shown in FIG. 4b, where it is evident that the protein lacking LITAF aa 164-180 did not shift the DNA (lane 13), whereas a shift was observed if LITAF aa 164-180 was present (lane 7, 10, and 16). These findings show that LITAF aa 164 to 180 binds to the hTNF-α promoter region.

ELISA of hTNF-α by Stimulation of Peptide

The data herein suggest that hLITAF aa 164-180 might be sufficient to induce TNF-α expression in monoytic cells. Therefore, peptides A, B, and C, were synthesized based on the amino acid sequence of hLITAF. Peptide HA, which did not correspond to a LITAF sequence, was also prepared and used as negative control. After pretreatment with PMA, peptides A, B, C, or HA were introduced into THP-1 cells using Chariot, as described herein, in concentrations of 1, 10, 100 ng/ml or 1 µg/ml. After 24 hours, culture supernatants were harvested and TNF-α was quantified by ELISA. As shown in FIG. 5, treatment with peptides A, C, or HA did not induce any significant TNF-α secretion. In contrast, peptide B increased TNF-α secretion by as much as 2.4 fold over unstimulated levels.

Analysis of Promoter Activity by Stimulation of LPS or Peptide A, B, or C

Figure 6A:
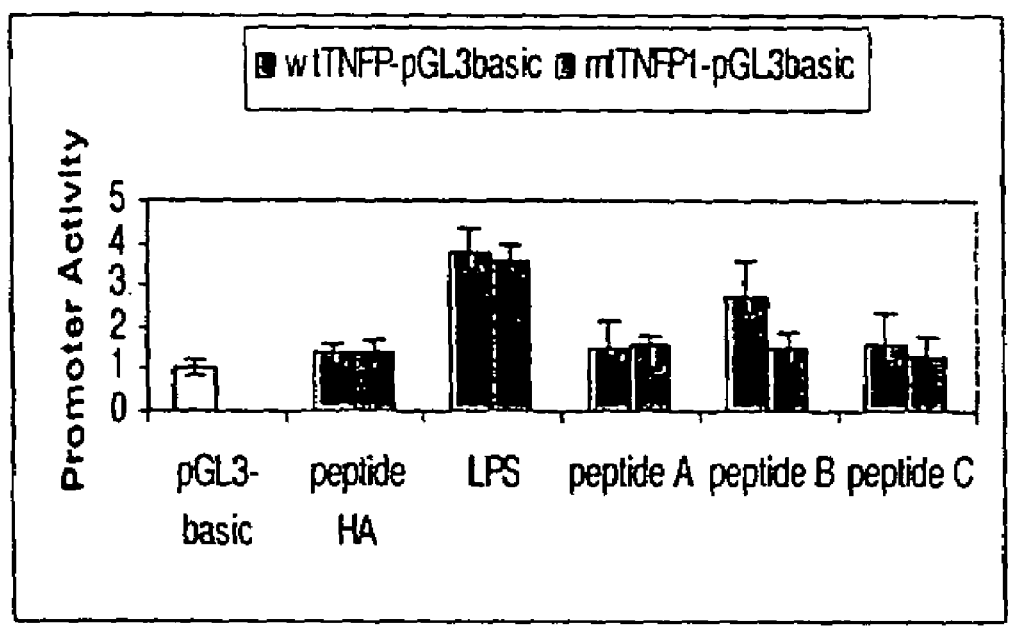
FIGS. 6a and 6b are graphical representations of the transcriptional activity of a series of deletion constructs of TNF-α promoter DNA.
Figure 6B:
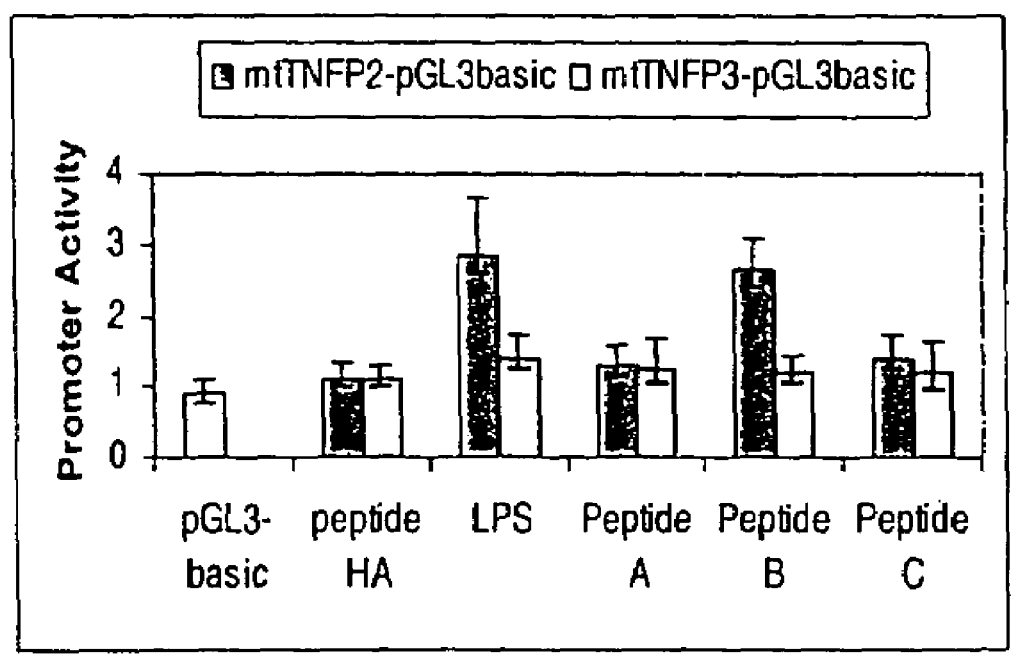

To determine whether the short sequence CTCCC (−515 to −511) in the hTNF-a promoter is responsible for hLITAF binding activity, a series of hTNF-α promoter/reporter constructs were cloned (see FIG. 1b) and individually transiently transfected into THP-1 cells. Cells were then stimulated by LPS, or transfected by Chariot-compounded peptide A, B, C, or HA. TNF-α promoter activity was subsequently analyzed using the luciferase assay. As shown in FIG. 6a, LPS similarly activated both the wild type full-length TNF-α promoters and TNF 1, and corresponding promoters lacking the LITAF binding site. In contrast, treatment with peptide A or C did not result in any significant increase in hTNF-α promoter activity. However, compared with HA-stimulated cells, peptide B caused approximately a 2 fold increase in luciferase expression induced by the wild type promoter. The mutant TNF-α promoter, which lacks the CTCCC motif, showed no appreciable induction by peptides A, B, or C (FIG. 6a). Subsequent studies were performed using luciferase reporter plasmids under the control of a small fragment of the hTNF-α promoter that contains or lacks the LITAF binding site (FIG. 1b). THP-1 cells were transiently transfected with these shorter reporter plasmids, and then treated with LPS or peptides A, B, C, or HA (FIG. 6b). It was observed that activation of this shorter reporter plasmid by LPS was strongly dependent on the presence of the LITAF binding site, with activation not observed in reporter plasmids lacking the LITAF binding site, consistent with data obtained using the full-length hTNF-α promoter (FIG. 6a). Furthermore, peptides A and C were unable to activate the reporter plasmids containing the binding site, whereas peptide B induced a 2.3 fold expression of luciferase in comparison with the HA control. Together, these studies support a role for LITAF in activation of the hTNF-α promoter by LPS. Furthermore, a peptide corresponding to the SQTWREPGAAGSPFHL fragment of the full-length LITAF peptide sequence possesses the ability to activate the hTNF-α promoter.

In summary, using a short reporter construct, a clear dependence of the CTCCC-containing region on promoter activation by LPS and an LITAF fragment was observed and, separately, that hLITAF aa 164-180 region is a domain capable of activating TNF-α gene expression. Together, these findings help to clarify the mechanism of hLITAF/hTNF-α interaction, and the manner by which hLITAF contributes to hTNF-α regulation. The elucidation of these mechanisms should help the design of new pharmacological approaches aimed at addressing TNF-related diseases.

Example 2

As described herein, the region within human LITAF (hLITAF) that specifically mediates DNA binding resides in the sequence corresponding to hLITAF aa 164-180 (i.e., peptide sequence SQTWREPGAAGSPFHL (SEQ ID NO: 5), and LITAF protein fragments corresponding to that area were determined to be sufficient to bind and activate the TNF-α promoter. As also described herein, the sequence motif CTCCC (−515 to −511), within the TNF-α promoter, binds to hLITAF aa 164-180. Several studies have shown that a known tumor suppressor gene, p53, participates in inducing apoptosis in response to a variety of stress stimuli, including ionizing radiation, cytotoxic agents, oxidative stress, and LPS (see Kinzler and Volgolstein, Nature 379: 19-20, 1996; Ko and Prives, Genes Dev. 10:1054-1072, 1996; Levine, A. J., Cell 88:323-33 1, 1997; and Munshi et al., J. Immunol. 168:5860-5866, 2002). Normally p53 functions as a transcription factor that regulates DNA repair, cell proliferation, and cell death. It has been shown to upregulate the apoptosis inducer BAX (Miyashita and Reed, Cell 80:293-299, 1995) and to down-regulate a competing cell survival signal, Bcl-2 (Adams and Cory, Science 281:1322-1326, 1998). The cyclin-dependent kinase inhibitor p21, involved in cell growth arrest, is also regulated by p53 (Brugoarolas et al, Nature 377:552-557, 1995; el-Deiry et al, Cell 75:817-825, 1993; Vousden and Lu, Nat. Rev. Cancer 2:594-604, 2002). Several studies have also indicated that the expression of p53 could be detected after prolonged (24 hrs), but not brief (6 hrs), treatment with LPS (Munshi et al., J. Immunol. 168:5860-5866, 2002; Xaus et al., Blood 95:3823-3831, 2000). However, it is also known that LITAF is induced after only 2-4 hrs of treatment with LPS (Myokai et al., Proc. Natl. Acad. Sci. USA 96: 4518-4523 (1999); Tang et al., Proc. Natl. Acad. Sci. USA, 100:4096-101, 2003) and that LITAF mRNA is markedly increased in p53-expressing cells (Polyak et al., Nature 389:300-305, 1997). However, the signaling pathway(s) whereby p53 induces apoptosis through TNF-α in response to LPS remain unclear. The following experiments described below were performed to determine the role of p53 in the expression of LITAF and what effect LPS had on LITAF expression.

LPS-Induced Timely Accumulation of p53 Protein and LITAF mRNA

Figure 7:
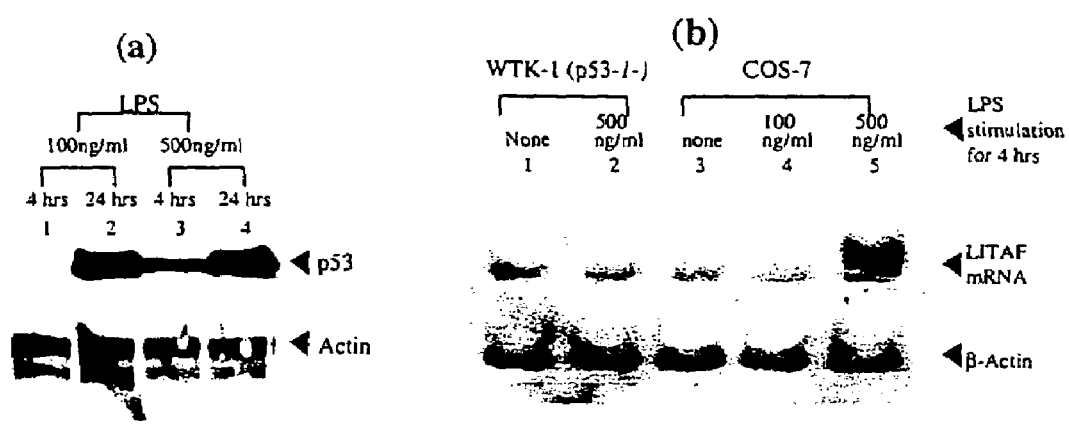
FIGS. 7a and 7b show the analysis of the accumulation of p53 and induction of LITAF mRNA.

The accumulation of p53 after LPS stimulation was investigated. The analysis of Western and Northern blots performed on LPS-stimulated COS-7 cells (wild-type p53) or WTK-1 cells (p53-deficient cell line) demonstrated that inducible p53 (FIG. 7a, lane 3) or LITAF transcript (FIG. 7b, lane 5) was detected after LPS treatment (500 ng/ml) for 4 hrs in COS-7 cells. LPS did not induce LITAF transcription in WTK-1 cells (FIG. 7b, lane 2). The findings suggest that p53-induced LITAF transcripts can be detected, with induction of LITAF following the accumulation of p53 after 500 ng/ml LPS treatment for 4 hrs.

Detection of DNA Fragmentation of Apoptotic COS-7 Cells

Figure 8:
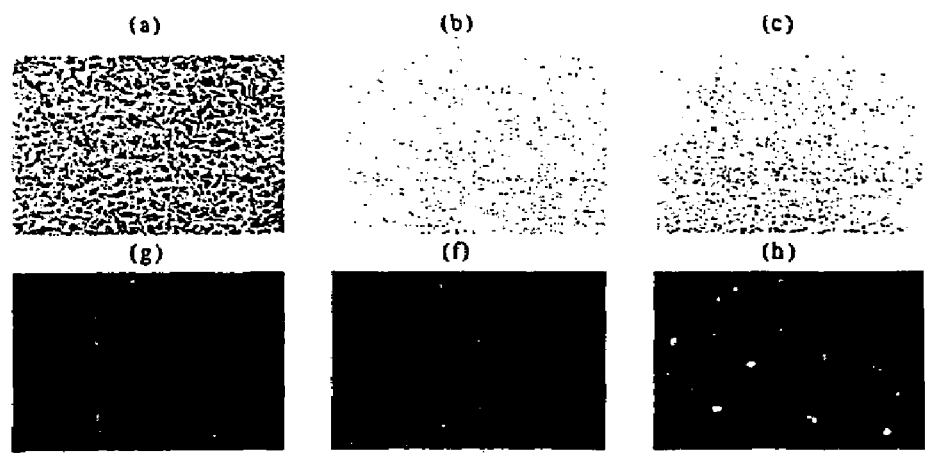
FIG. 8 depicts the TUNEL analysis of DNA fragmentation of apoptotic COS-7 cells in response to LPS. After LPS stimulation, cells were fixed in 4% methanol-free formaldehyde solution for 30 min at room temperature, then permeated with 0.1% Triton X-100 for 2 min at 4° C. After washing with PBS, the samples were stained according to the manufacturer's recommended protocol for TUNEL (Promega.). The fragmentation of apoptotic COS-7 cell nuclei was analyzed by fluorescence microscopy (panels g, f, or h). The corresponding field was also observed by standard phase contrast microscopy (panels a, b, or c).

Since the induction of LITAF follows the accumulation of p53 (FIG. 7a), the DNA fragmentation of apoptotic COS-7 cells after 4 hrs with LPS stimulation was investigated. It was found that TUNEL-positive cells (green color), depicting apoptotic cells, significantly increased after treatment with 500 ng/ml LPS for at least 4 hrs. In contrast, stimulation without LPS (FIG. 8g) or with 100 ng/ml of LPS (FIG. 8f) did not induce apoptosis.

Identification of LITAF Binding Activity in the TNF-α Promoter

The amino acid sequence of hLITAF, (GenBank: U77396) with aa 152-228 indicated by an underline, is:

MSVPGPYQAATGPSSAPSAPPSYEETVAVNSYYPTPPAPMPGPTTG

LVTGPDGKGMNPPSYYTQPAPIPNNNPITVQTVYVQHPITFLDRPIQMCC

PSCNKMIVSQLSYNAGALTWLSCGSLCLLGVHSGLLLHPLLRGCPAGRGP

LLSQLQSSPGHLQAFVGLSQTWREPGAAGSPFHLSSSFTPGGGSALVVSP

LQGAHLHVFFWGEYVAKLTNLQTPEIAAWSRA.
(SEQ ID NO: 1)

Figure 9:
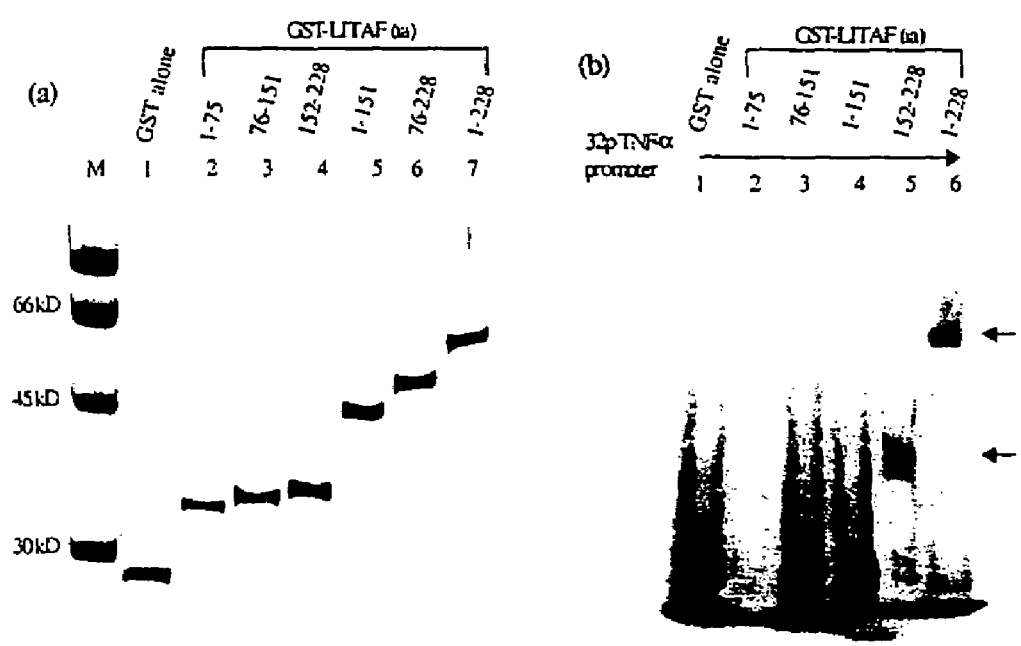
FIGS. 9a and 9b show the interaction of in vitro translated $^{32}$P-labeled TNF-α promoter and GST-LITAF derivatives.

A DNA fragment representing the LITAF full length sequence (228 amino acids) was subcloned into the pGEX4T-1 vector (Pharmacia). GST-LITAF recombinant plasmid was then transformed into competent BL21 cells. The GST-LITAF fusion protein was induced with IPTG and purified with glutathione-Sepharose 4B beads (Pharmacia). Using these stable GST-LITAF fusion proteins (FIG. 9a), a set of LITAF deletion mutants was examined, representing regions aa 1-76, 76-151, 1-151, 152-228 and 1-228 (full length), for their ability to interact with in vitro-translated, $^{32}$P-labeled 20 TNF-α promoter DNA (FIG. 9b). As shown in FIG. 3, both fusion proteins aa 152-228 (lane 5) and 1-228 (lane 6) shifted the DNA band, as indicated by arrows. Thus, these data suggest that LITAF region aa 152-228 participates in TNF-α binding.

Detection of LITAF Function by Luciferase Assay

Figure 10:
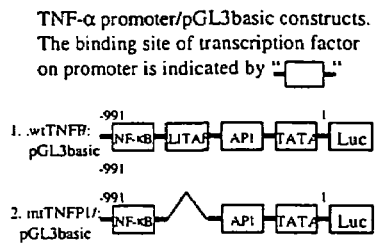
FIG. 10 is a graphical representation of the analysis of LITAF function in luciferase reporter constructs. The series of TNF-α promoter DNA fragments were subcloned into the pGL3 basic vector (Pharmacia), a promoterless and enhancerless luciferase reporter gene. One construct, named wtTNFβ, contained TNF-α promoter from −991 to 1. Another one, mtTNFβ1, was a mutant inserted with the promoter from −991 to 1, but lacking the LITAF binding site. WTK-1 cells (grown to 85% confluence) in a 6-well plate at 1.2×10$^5$ cells/well were co-transfected with 1 μg DNAs including pCMV-LITAF recombinant vector, pVMVβ-gal and pGL3 basic as control by Fugene 6 (Roche Molecular Biochemicals) for 3 hrs, washed with PBS twice, then individually stimulated with LPS or Chariot/peptide complex of 100 ng/ml peptide B (peptide fragment of LITAF representing aa 152-228) or HA as control for 3 hrs, washed with PBS, incubated at 37° C., 5% CO$_2$, o/n. The β-galactosidase gene was included in all transfections. The cells were harvested and lysed approximately 12 hrs after transfection. The promoter activity from each lysate sample was measured using the luciferase reporter assay system (Promega) and normalized to β-gal expression in the same sample, as described in the methods section below.
Figure 10:
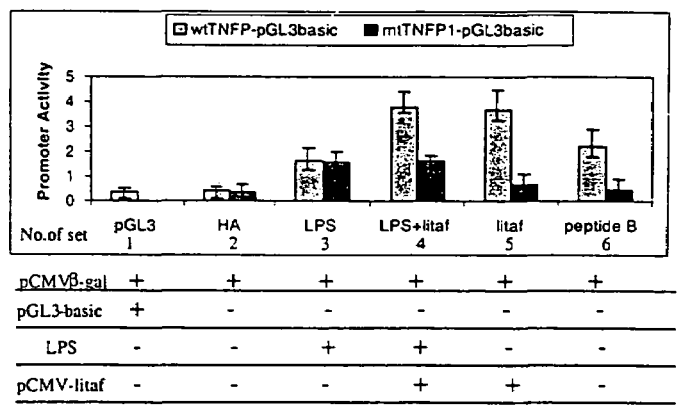

The activation of TNF-α gene expression by LITAF was investigated. WTK-1 cells were chosen as a host for a luciferase reporter plasmid as this cell line contains a mutant p53 (Li et al., Proc. Natl. Acad. Sci. USA 99:10364-10369, 2002). It was thought that the induction of LITAF is p53-dependent, and that once induced, LITAF protein binds to the TNF-α promoter, and subsequently mediates the regulation of TNF-α gene expression. As shown in FIG. 10, cells transfected with wild-type or mutant TNF-α promoter/reporter plasmids were similarly activated by LPS (FIG. 10, set 3) Since the region −991 to +1 in the TNF-α promoter is known to contain not only the LITAF binding site, but also sites for NF-κB, API and others (Amar and Han, Applied Genomics and Proteomics 1:31-44, 2002), it seems reasonable that these transcription factors were induced by LPS and bound to the TNF promoter to regulate its expression. In addition, it suggests that LITAF was poorly induced due to the absence of p53 in this cell line. Furthermore, overexpression of exogenous LITAF alone, without LPS stimulation, induced a 2.5-fold increase in promoter activity in the presence of the CTCCC TNF binding site (FIG. 5, set 5). These findings suggest that the induction of LITAF is dependent on p53 in response to LPS, and that LITAF can regulate TNF-α gene expression.

All publications and patents cited in this specification are hereby incorporated by reference herein as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated peptide fragment of SEQ ID NO: 1, said peptide fragment comprising the sequence set forth in SEQ ID NO: 5, wherein said fragment has a deletion of one or more of the N-terminal residues set forth in SEQ ID NO. 1 and is capable of promoting transcription of tumor necrosis factor-alpha (TNF-α) by binding to a region of the TNF-α promoter.

2. The peptide fragment of claim 1, wherein said TNF-α is human.

3. An isolated peptide fragment comprising the sequence set forth in SEQ ID NO: 5, wherein said fragment lacks one or more of the C-terminal residues set forth in SEQ ID NO. 1 and is capable of promoting transcription of tumor necrosis factor-alpha (TNF-α) by binding to a region of the TNF-α promoter.

4. The peptide fragment of claim 3, wherein said TNF-α is human.

5. An isolated peptide fragment comprising the sequence set forth in SEQ ID NO: 5, wherein said fragment lacks one or more of the N-terminal and C-terminal residues set forth in SEQ ID NO. 1 and is capable of promoting transcription of tumor necrosis factor-alpha (TNF-α) by binding to a region of the TNF-α promoter.

6. The peptide fragment of claim 5, wherein said TNF-α is human.

7. An isolated peptide fragment, wherein said fragment consists of the sequence set forth in SEQ ID NO: 5 and is capable of promoting transcription of tumor necrosis factor-alpha (TNF-α) by binding to a region of the TNF-α promoter.

8. The peptide fragment of claim 7, wherein said TNF-α is human.

9. An isolated peptide fragment, wherein said fragment consists of the sequence set forth in SEQ ID NO: 3 and is capable of promoting transcription of tumor necrosis factor-alpha (TNF-α) by binding to a region of the TNF-α promoter.

10. The peptide fragment of claim 9, wherein said TNF-α is human.

* * * * *

SEQUENCE LISTING

```
<160> NUMBER OF SEQ ID NOS: 2

<210> SEQ ID NO 1
<211> LENGTH: 228
<212> TYPE: PRT
<213> ORGANISM: Homo sapiens

<400> SEQUENCE: 1

Met Ser Val Pro Gly Pro Tyr Gln Ala Ala Thr Gly Pro Ser Ser Ala
 1               5                  10                  15

Pro Ser Ala Pro Pro Ser Tyr Glu Glu Thr Val Ala Val Asn Ser Tyr
            20                  25                  30

Tyr Pro Thr Pro Pro Ala Pro Met Pro Gly Pro Thr Thr Gly Leu Val
        35                  40                  45
```

```
Thr Gly Pro Asp Gly Lys Gly Met Asn Pro Ser Tyr Tyr Thr Gln
    50              55                  60

Pro Ala Pro Ile Pro Asn Asn Asn Pro Ile Thr Val Gln Thr Val Tyr
65              70                  75                  80

Val Gln His Pro Ile Thr Phe Leu Asp Arg Pro Ile Gln Met Cys Cys
                85                  90                  95

Pro Ser Cys Asn Lys Met Ile Val Ser Gln Leu Ser Tyr Asn Ala Gly
            100                 105                 110

Ala Leu Thr Trp Leu Ser Cys Gly Ser Leu Cys Leu Leu Gly Val His
        115                 120                 125

Ser Gly Leu Leu Leu His Pro Leu Leu Arg Gly Cys Pro Ala Gly Arg
    130                 135                 140

Gly Pro Leu Leu Ser Gln Leu Gln Ser Ser Pro Gly His Leu Gln Ala
145                 150                 155                 160

Phe Val Gly Leu Ser Gln Thr Trp Arg Glu Pro Gly Ala Ala Gly Ser
                165                 170                 175

Pro Phe His Leu Ser Ser Ser Phe Thr Pro Gly Gly Ser Ala Leu
            180                 185                 190

Val Val Ser Pro Leu Gln Gly Ala His Leu His Val Phe Phe Trp Gly
    195                 200                 205

Glu Tyr Val Ala Lys Leu Thr Asn Leu Gln Thr Pro Glu Ile Ala Ala
    210                 215                 220

Trp Ser Arg Ala
225
```

<210> SEQ ID NO 2
<211> LENGTH: 1773
<212> TYPE: DNA
<213> ORGANISM: Homo sapiens

<400> SEQUENCE: 2

```
gtttctctcc ctgcccccgc gacttcgcgc aagatccggg aaggacaccc gaggcccctg      60
ggagaccctg gggaggtgaa agtcagagag cgaagcgggc cgtggcccct aggcctgacc     120
cctccccgcg gggtaaggcg ggcaccccgc gagcgcaggg gtcctcttac tgctgatggc     180
acccagctct gggcccagac gccgctcacc gtccaccgcc ggtgctgggt aaaatgtcgg     240
ttccaggacc ttaccaggcg ccactgggc cttcctcagc accatccgca cctccatcct     300
atgaagagac agtggctgtt aacagttatt accccacacc tccagctccc atgcctgggc     360
caactacggg gcttgtgacg gggcctgatg ggaagggcat gaatcctcct tcgtattata     420
cccagccagc gcccatcccc aataacaatc caattaccgt gcagacggtc tacgtgcagc     480
accccatcac cttttggac cgccctatcc aaatgtgttg tccttcctgc aacaagatga     540
tcgtgagtca gctgtcctat aacgccggtg ctctgacctg gctgtcctgc gggagcctgt     600
gcctgctggg ggtgcatagc gggctgctgc ttcatcccct tctgcgtgga tgccctgcag     660
gacgtggacc attactgtcc caactgcaga gctctcctgg gcacctacaa gcgtttgtag     720
gactcagcca gacgtggagg gagccgggtg ccgcaggaag tcctttccac ctctcatcca     780
gcttcacgcc tggtggaggt tctgccctgg tggtctcacc tctccagggg gcccaccttc     840
atgtcttctt ttgggggggaa tacgtcgcaa aactaacaaa tctccaaacc ccagaaattg     900
ctgcttggag tcgtgcatag gacttgcaaa gacattcccc ttgagtgtca gttccacggt     960
ttcctgcctc cctgagaccc tgagtcctgc catctaactg tgatcattgc cctatccgaa    1020
```

-continued

| | | | | | |
|---|---|---|---|---|---|
| tatcttcctg | tgatctgcca | tcagtggctc | ttttttcctg | cttccatggg | cctttctggt | 1080 |
| ggcagtctca | aactgagaag | ccacagttgc | cttattttg | aggctgttct | gcccagagct | 1140 |
| cggctgaacc | agcctttagt | gcctaccatt | atcttatccg | tctcttcccg | tccctgatga | 1200 |
| caaagatctt | gccttacaga | ctttacaggc | ttggctttga | gattctgtaa | ctgcagactt | 1260 |
| cattagcaca | cagattcact | ttaatttctt | aattttttt | ttaaatacaa | ggaggggct | 1320 |
| attaacaccc | agtacagaca | tatccacaag | gtcgtaaatg | catgctagaa | aaatagggct | 1380 |
| ggatcttatc | actgccctgt | ctccccttgt | ttctctgtgc | cagatcttca | gtgccccttt | 1440 |
| ccatacaggg | atttttttct | catagagtaa | ttatatgaac | agtttttatg | acctccttt | 1500 |
| ggtctgaaat | acttttgaac | agaatttctt | tttttaaaa | aaaaacagag | atggggtctt | 1560 |
| actatgttgc | ccaggctggt | gtcgaactcc | tgggctcaag | cgatccttct | gccttggcct | 1620 |
| cccgaagtgc | tgggattgca | ggcataagct | accatgctgg | gcctgaacat | aatttcaaga | 1680 |
| ggaggattta | taaaaccatt | ttctgtaatc | aaatgattgg | tgtcattttc | ccatttgcca | 1740 |
| atgtagtctc | acttaaaaaa | aaaaaaaaaa | aaa | | | 1773 |